United States Patent
Islam et al.

(10) Patent No.: US 7,342,656 B2
(45) Date of Patent: Mar. 11, 2008

(54) DYNAMICALLY VARIABLE SEPARATION AMONG NANOPARTICLES FOR NANO-ENHANCED RAMAN SPECTROSCOPY (NERS) MOLECULAR SENSING

(75) Inventors: M. Saif Islam, Sacramento, CA (US); Shih-Yuan Wang, Palo Alto, CA (US); R. Stanley Williams, Portola Valley, CA (US); Philip J. Kuekes, Menlo Park, CA (US); Wei Wu, Mountain View, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 97 days.

(21) Appl. No.: 11/252,134

(22) Filed: Oct. 17, 2005

(65) Prior Publication Data
US 2007/0086001 A1    Apr. 19, 2007

(51) Int. Cl.
G01J 3/44 (2006.01)
G01N 21/65 (2006.01)
(52) U.S. Cl. ..................................... 356/301
(58) Field of Classification Search ................. 356/301
See application file for complete search history.

(56) References Cited

U.S. PATENT DOCUMENTS

| | | |
|---|---|---|
| 4,674,878 A | 6/1987 | Vo-Dinh |
| 4,944,985 A | 7/1990 | Alexander et al. |
| 5,017,007 A | 5/1991 | Milne et al. |
| 5,139,334 A | 8/1992 | Clarke |
| 5,242,828 A | 9/1993 | Bergstrom et al. |
| 5,255,067 A | 10/1993 | Carrabba et al. |
| 5,527,712 A | 6/1996 | Sheehy |
| 5,609,907 A | 3/1997 | Natan |
| 5,646,039 A | 7/1997 | Northrup et al. |

(Continued)

FOREIGN PATENT DOCUMENTS

WO    WO 98/10289 A1    3/1998

(Continued)

OTHER PUBLICATIONS

Collier, C.P., et al., "Reversible Tuning of Silver Quantum Dot Monolayers Through the Meltal-Insulator Transition," Science, vol. 277, pp. 1978-1981, Sep. 29, 1997.

(Continued)

Primary Examiner—F. L. Evans

(57) ABSTRACT

A NERS-active structure includes a deformable, active nanoparticle support structure for supporting a first nanoparticle and a second nanoparticle that is disposed proximate the first nanoparticle. The nanoparticles each comprise a NERS-active material. The deformable, active nanoparticle support structure is configured to vary the distance between the first nanoparticle and the second nanoparticle while performing NERS. Various active nanoparticle support structures are disclosed. A NERS system includes such a NERS-active structure, a radiation source for generating radiation scatterable by an analyte located proximate the NERS-active structure, and a radiation detector for detecting Raman scattered radiation scattered by the analyte. A method for performing NERS includes providing such a NERS-active structure, providing an analyte at a location proximate the NERS-active structure, irradiating the NERS-active structure and the analyte with radiation, varying the distance between the nanoparticles, and detecting Raman scattered radiation scattered by the analyte.

31 Claims, 11 Drawing Sheets

U.S. PATENT DOCUMENTS

| | | |
|---|---|---|
| 5,772,905 A | 6/1998 | Chou |
| 5,837,552 A | 11/1998 | Cotton et al. |
| 5,885,753 A | 3/1999 | Crooks et al. |
| 6,025,202 A | 2/2000 | Natan |
| 6,149,868 A | 11/2000 | Natan et al. |
| 6,165,911 A | 12/2000 | Calveley |
| 6,242,264 B1 | 6/2001 | Natan et al. |
| 6,248,674 B1 | 6/2001 | Kamins et al. |
| 6,291,924 B1 | 9/2001 | Lau et al. |
| 6,365,059 B1 | 4/2002 | Pechenik |
| 6,406,777 B1 | 6/2002 | Boss et al. |
| 6,432,740 B1 | 8/2002 | Chen |
| 6,579,721 B1 | 6/2003 | Natan et al. |
| 6,623,977 B1 | 9/2003 | Farquharson et al. |
| 6,649,683 B2 | 11/2003 | Bell |
| 6,773,616 B1 | 8/2004 | Chen et al. |
| 6,808,954 B2 | 10/2004 | Ma et al. |
| 6,861,263 B2 | 3/2005 | Natan |
| 7,008,796 B2 | 3/2006 | Wohlstadter et al. |
| 2003/0030800 A1 | 2/2003 | Golden et al. |
| 2003/0120137 A1 | 6/2003 | Pawluczyk |
| 2003/0157732 A1 | 8/2003 | Baker et al. |
| 2003/0186240 A1 | 10/2003 | Su et al. |
| 2003/0231304 A1 | 12/2003 | Chan et al. |
| 2004/0077844 A1 | 4/2004 | Jacobson et al. |
| 2004/0126790 A1 | 7/2004 | Su et al. |
| 2004/0135997 A1 | 7/2004 | Chan et al. |
| 2004/0142484 A1 | 7/2004 | Berlin et al. |
| 2005/0084980 A1 | 4/2005 | Koo et al. |
| 2005/0110990 A1 | 5/2005 | Koo et al. |
| 2005/0147979 A1 | 7/2005 | Koo et al. |
| 2005/0264817 A1 | 12/2005 | Harvard et al. |
| 2006/0028908 A1 | 2/2006 | Suriadi et al. |
| 2006/0183236 A1 | 8/2006 | Berlin et al. |
| 2006/0240573 A1 | 10/2006 | Kao et al. |

FOREIGN PATENT DOCUMENTS

| | | |
|---|---|---|
| WO | WO 2004/059279 A2 | 7/2004 |

OTHER PUBLICATIONS

Garcia-Vidal, F.J., et al., "Collective Theory for Surface Enhanced Raman Scattering," Physical Review Letters, vol. 77, No. 6, pp. 1163-1166. Aug. 5, 1996.

Lu, Yu, et al., "High-Density Silver Nanoparticle Film with Temperature-Controllable Interparticle Spacing for a Tunable Surface Enhanced Raman Scattering Substrate," Nano Lett., vol. 5, No. 1, pp. 5-9, 2005.

Nie, Shuming, et al., "Probing Single Molecules and Single Nanoparticles by Surface-Enhanced Raman Scattering." Science, vol. 275, pp. 1102-1106, Feb. 21, 1997.

Michaels, et al., Surface Enhanced Raman Spectroscopy of Individual Rhodamine 6G Molecules on Large Ag Nanocrystals, J. Am. Chem. Soc. Oct. 14, 1999, 121, pp. 9932-9939.

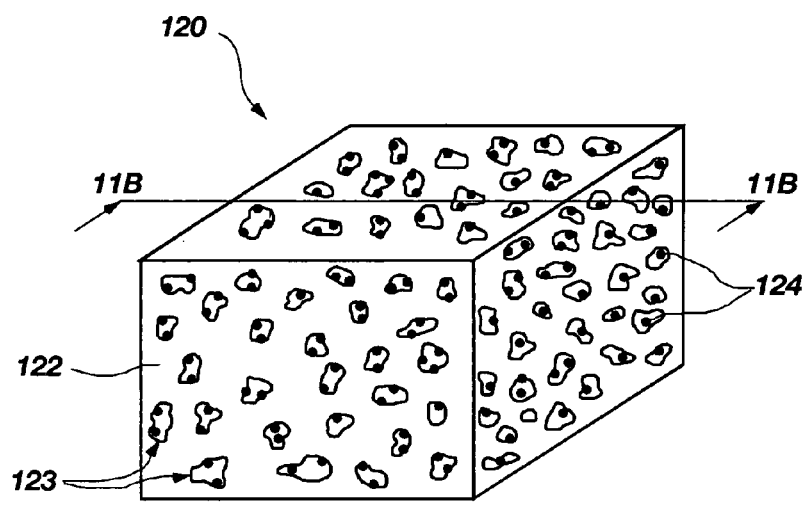
FIG. 11A
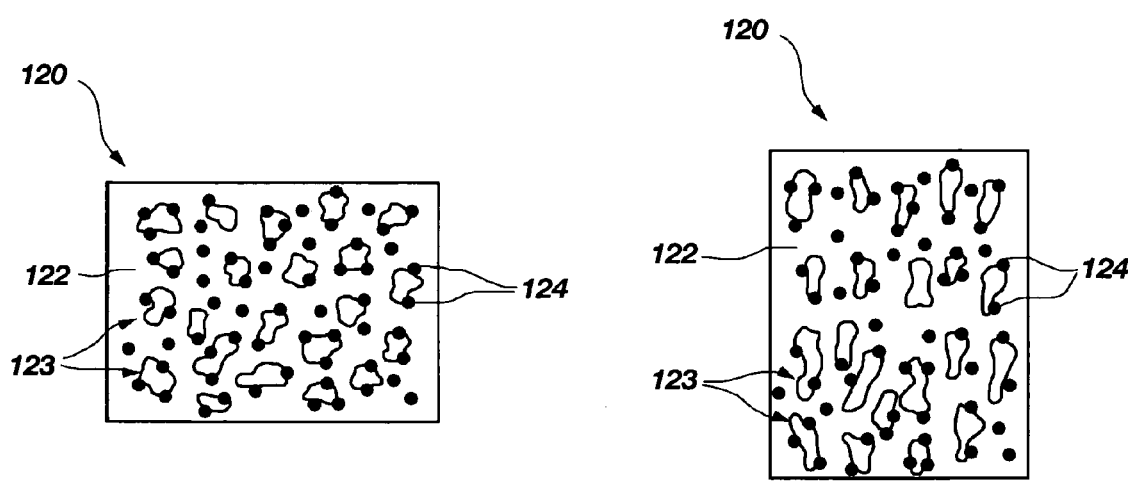
FIG. 11B
FIG. 11C

DYNAMICALLY VARIABLE SEPARATION AMONG NANOPARTICLES FOR NANO-ENHANCED RAMAN SPECTROSCOPY (NERS) MOLECULAR SENSING

FIELD OF THE INVENTION

The present invention relates to nano-enhanced Raman spectroscopy (NERS). More particularly, the invention relates to NERS-active structures for use as analyte substrates in NERS, methods for forming NERS-active structures, NERS systems, and methods for performing NERS using NERS-active structures.

BACKGROUND OF THE INVENTION

Raman spectroscopy is a well-known technique for analyzing molecules or materials. In conventional Raman spectroscopy, high intensity monochromatic radiation provided by a radiation source, such as a laser, is directed onto an analyte (or sample) that is to be analyzed. In NERS, the wavelength of the incident radiation typically is varied over a range of wavelengths within or near the visible region of the electromagnetic spectrum. A majority of the photons of the incident radiation are elastically scattered by the analyte. In other words, the scattered photons have the same energy, and thus the same wavelength, as the incident photons. However, a very small fraction of the photons are inelastically scattered by the analyte. Typically, only about 1 in $10^7$ of the incident photons are inelastically scattered by the analyte. These inelastically scattered photons have a different wavelength than the incident photons. This inelastic scattering of photons is termed "Raman scattering". The Raman scattered photons can have wavelengths less than, or, more typically, greater than the wavelength of the incident photons.

When an incident photon collides with the analyte, energy can be transferred from the photon to the molecules or atoms of the analyte, or from the molecules or atoms of the analyte to the photon. When energy is transferred from the incident photon to the analyte, the Raman scattered photon will have a lower energy and a corresponding longer wavelength than the incident photon. These Raman scattered photons having lower energy than the incident photons are collectively referred to in Raman spectroscopy as the "Stokes radiation." A small fraction of the analyte molecules or atoms can be in an energetically excited state when photons are incident thereon. When energy is transferred from the analyte to the incident photon, the Raman scattered photon will have a higher energy and a corresponding shorter wavelength than the incident photon. These Raman scattered photons having higher energy than the incident photons are commonly referred to in Raman spectroscopy as the "anti-Stokes radiation." The Stokes radiation and the anti-Stokes radiation collectively are referred to as the Raman scattered radiation or the Raman signal.

The Raman scattered radiation is detected by a detector that typically includes a wavelength-dispersive spectrometer and a photomultiplier for converting the energy of the impinging photons into an electrical signal. The characteristics of the electrical signal are at least partially a function of both the energy of the Raman scattered photons as evidenced by their wavelength, frequency, or wave number, and the number of the Raman scattered photons as evidenced by the intensity of the Raman scattered radiation. The electrical signal generated by the detector can be used to produce a spectral graph illustrating the intensity of the Raman scattered radiation as a function of the wavelength of the Raman scattered radiation. Analyte molecules and materials generate unique Raman spectral graphs. The unique Raman spectral graph obtained by performing Raman spectroscopy can be used for many purposes including identification of an unknown analyte, or determination of physical and chemical characteristics of a known analyte.

Raman scattering of photons is a weak process. As a result, powerful, costly laser sources typically are used to generate high intensity incident radiation to increase the intensity of the weak Raman scattered radiation for detection. Surface enhanced Raman spectroscopy (SERS) is a technique that allows for enhancement of the intensity of the Raman scattered radiation relative to conventional Raman spectroscopy. In SERS, the analyte molecules typically are adsorbed onto or placed adjacent to what is often referred to as a SERS-active structure. SERS-active structures typically include a metal surface or structure. Interactions between the analyte and the metal surface cause an increase in the intensity of the Raman scattered radiation. The mechanism by which the intensity of the Raman scattered radiation is enhanced is not completely understood. Two main theories of enhancement mechanisms have been presented in the literature: electromagnetic enhancement and chemical enhancement. For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," J. Am. Chem. Soc. 121, 9932-39 (1999).

Several types of metallic structures have been employed in SERS techniques to enhance the intensity of Raman scattered radiation that is scattered by analyte molecules adjacent thereto. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface made from gold or silver can enhance the Raman scattering intensity by factors of between $10^3$ and $10^6$.

Recently, Raman spectroscopy has been performed employing randomly oriented nanostructures, such as nanometer scale needles, particles, and wires, as opposed to a simple roughened metallic surface. This process will be referred to hereinafter as nano-enhanced Raman spectroscopy (NERS). The intensity of the Raman scattered photons from a molecule adsorbed on such a metal surface can be increased by factors as high as $10^{16}$. At this level of sensitivity, NERS has been used to detect single molecules. Detecting single molecules with high sensitivity and molecular specificity is of great interest in the fields of chemistry, biology, medicine, pharmacology, and environmental science.

It is unknown what metallic particle configurations, including particle size, particle shape and particle spacing will enhance the intensity of Raman scattered radiation most effectively for any given analyte. Therefore, the metallic particles used in NERS typically have a variety of sizes and are randomly oriented and positioned to provide a wide range of particle configurations. When such a structure is used to perform NERS, typically only a few small, localized areas of the NERS-active structure provide a configuration that will substantially enhance the Raman scattering of radiation by the analyte molecules disposed in those areas. Other areas of the NERS-active structure do not substantially enhance the intensity of Raman scattered radiation and, therefore, do not contribute to the utility of the NERS-active structure. In addition, if the particle configuration provided by a NERS-active structure does not significantly enhance the intensity of Raman scattered radiation for a given analyte, a new NERS-active structure having a different particle configuration must be provided.

Accordingly, there is a need for a NERS-active structure that provides spacing between metallic particles that can be varied or changed to optimize the enhancement of the intensity of Raman scattered radiation scattered by an analyte in the vicinity of the metallic particles.

BRIEF SUMMARY OF THE INVENTION

The present invention relates to nano-enhanced Raman spectroscopy (NERS). More particularly, the invention relates to NERS-active structures for use as analyte substrates in NERS, methods for forming NERS-active structures, NERS systems, and methods for performing NERS using NERS-active structures.

In one aspect, the present invention includes a NERS-active structure that includes a deformable, active nanoparticle support structure for supporting a first nanoparticle comprising a NERS-active material and a second nanoparticle comprising a NERS-active material. The second nanoparticle is disposed proximate the first nanoparticle and separated from the first nanoparticle by a distance. The active nanoparticle support structure is configured to vary the distance between the first nanoparticle and the second nanoparticle while performing NERS.

In another aspect, the present invention includes a NERS system that includes a NERS-active structure, a radiation source for generating radiation scatterable by an analyte located proximate the NERS-active structure, and a radiation detector for detecting Raman scattered radiation scattered by the analyte. The NERS-active structure includes a deformable, active nanoparticle support structure for supporting a first nanoparticle and a second nanoparticle. The first nanoparticle and the second nanoparticle include a NERS-active material. The second nanoparticle is disposed proximate the first nanoparticle and separated from the first nanoparticle by a distance. The active nanoparticle support structure is configured to vary the distance between the first nanoparticle and the second nanoparticle while performing NERS.

In yet another aspect, the present invention includes a method for performing NERS that includes providing a NERS-active structure, providing an analyte at a location proximate the NERS-active structure, irradiating the NERS-active structure and the analyte with radiation, varying the distance between the first nanoparticle and the second nanoparticle, and detecting Raman scattered radiation scattered by the analyte. Providing a NERS-active structure includes providing a first nanoparticle comprising a NERS-active material, providing a second nanoparticle comprising a NERS-active material, the second nanoparticle being disposed proximate the first nanoparticle and separated from the first nanoparticle by a distance, and providing an active nanoparticle support structure for supporting the first nanoparticle and the second nanoparticle. The active nanoparticle support structure is configured to vary the distance between the first nanoparticle and the second nanoparticle.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIG. 11A is a perspective view of an exemplary NERS-active structure that embodies teachings of the present invention and that includes nanoparticles disposed on a deformable substrate;

FIG. 11B is a cross sectional view of the NERS-active structure shown in FIG. 11A taken along section line 11B-11B therein;

FIG. 11C is a view like that of FIG. 11B showing the deformable substrate in a deformed state;

DETAILED DESCRIPTION OF THE INVENTION

The present invention relates to nano-enhanced Raman spectroscopy (NERS). More particularly, the invention relates to NERS-active structures for use as analyte substrates in NERS, methods for forming NERS-active structures, NERS systems, and methods for performing NERS using NERS-active structures.

The term "NERS-active material" as used herein means a material that, when formed into appropriate geometries or configurations, is capable of increasing the number of Raman scattered photons that are scattered by a molecule when the molecule is located proximate to that material, and the molecule and material are subjected to electromagnetic radiation. NERS-active materials can be used to form NERS-active structures. NERS-active materials include, but are not limited to, silver, gold, and copper.

The term "NERS-active structure" as used herein means a structure that is capable of increasing the number of Raman scattered photons that are scattered by a molecule when the molecule is located proximate to that structure and the molecule and structure are subjected to electromagnetic radiation.

The term "nanoparticle" as used herein means a particle of any shape having cross-sectional dimensions of less than about 100 nanometers. Examples of nanoparticles include, but are not limited to, nanodots, nanowires, nanocolumns, and nanospheres.

The term "analyte" as used herein means any molecule, molecules, material, or substance that is to be analyzed by NERS.

The term "elastic deformation" as used herein means nonpermanent deformation of an object that is induced by a force or load. An elastically deformed object returns to its original shape when the force or load is removed.

The illustrations presented herein are not meant to be actual views of any particular NERS-active structure or system, but are merely idealized representations which are employed to describe the present invention. Additionally, elements common between figures retain the same numerical designation.

NERS-active structures that include nanoparticles formed from a NERS-active material can be provided wherein the distance or spacing between the nanoparticles is selectively variable while performing NERS by modifying known structures for microelectromechanical system (MEMS) devices, such as a MEMS resonator. MEMS resonators typically are used in technical fields other than NERS to generate electrical signals or to filter electrical signals. Many structures of known MEMS resonators can be adapted to provide a NERS-active structure that includes an active nanoparticle support structure that is configured to selectively vary the distance between nanoparticles while performing NERS. Nanoparticles formed from a NERS-active material can be provided at various locations on the MEMS devices. The dimensions of known MEMS devices can be reduced if necessary to provide a NERS-active structure that can be used to vary the distance between adjacent nanoparticles thereon by tens of nanometers.

Figure 1A:
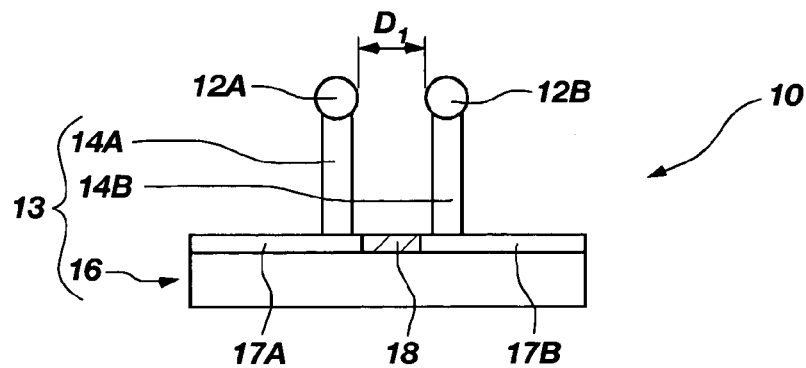
FIG. 1A is a side view of an exemplary NERS-active structure that embodies teachings of the present invention and that includes nanoparticles disposed on cantilever members.
Figure 1B:
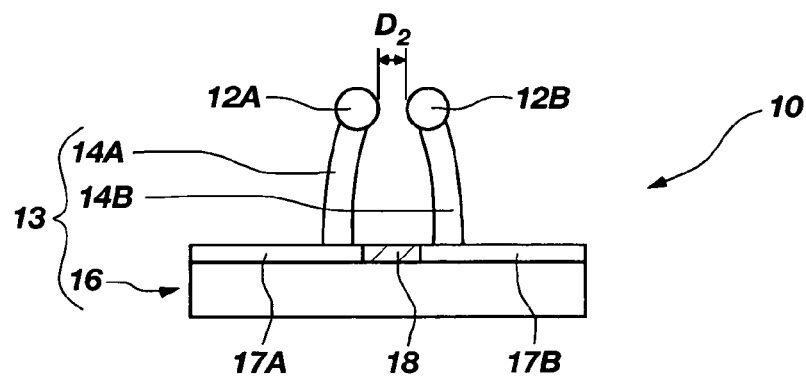
FIG. 1B is a side view of the exemplary NERS-active structure shown in FIG. 1A showing the cantilever members in a deflected position.
Figure 1C:
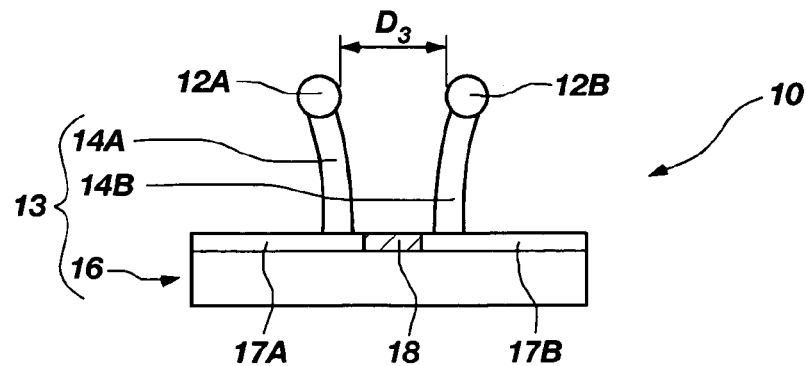
FIG. 1C is a side view of the exemplary NERS-active structure shown in FIG. 1A showing the cantilever members in another deflected position.

An exemplary NERS-active structure 10 that embodies teachings of the present invention is shown in FIGS. 1A-1C. The NERS-active structure 10 includes a first nanoparticle 12A and a second nanoparticle 12B. The first nanoparticle 12A is disposed on an end of an conductive, elongated first cantilever member 14A. An opposite end of the first cantilever member 14A is attached to a first conductive region 17A on a substrate 16. The second nanoparticle 12B is disposed on an end of a conductive, elongated second cantilever member 14B. An opposite end of the second cantilever member 14B is attached to a second conductive region 17B on the substrate 16. The first conductive region 17A on the substrate 16 is electrically isolated from the second conductive region 17B by an electrically insulating region 18 on the substrate 16.

The substrate 16 can be formed from, for example, a crystalline or polycrystalline silicon wafer. The first nanoparticle 12A and the second nanoparticle 12B are formed from a NERS-active material. The first conductive region 17A, the second conductive region 17B, the first cantilever member 14A, and the second cantilever member 14B are formed from a material that can conduct electrical charge, such as, for example, a metal or a semiconductive material, such as silicon, germanium, doped silicon or doped germanium.

Electrodes (not shown) may be formed on the first conductive region 17A and the second conductive region 17B of the substrate 16 for electrically charging the first nanoparticle 12A and the second nanoparticle 12B.

In this configuration, an active nanoparticle support structure 13 for supporting the first nanoparticle 12A and the second nanoparticle 12B is provided by the first cantilever member 14A, the second cantilever member 14B, and the substrate 16.

The first nanoparticle 12A and the second nanoparticle 12B are shown in a first position in FIG. 1A in which the first nanoparticle 12A and the second nanoparticle 12B are separated by a first distance $D_1$. In this position, the first cantilever member 14A and the second cantilever member 14B are substantially straight and extend from a surface of the substrate 16 in directions substantially parallel to one another. The first nanoparticle 12A and the second nanoparticle 12B will assume the first position shown in FIG. 1A when the first nanoparticle 12A and the second nanoparticle 12B are not significantly electrically charged.

If the first nanoparticle 12A and the second nanoparticle 12B are electrically charged with opposite charge (i.e., either the first nanoparticle 12A or the second nanoparticle 12B is negatively charged and the other nanoparticle is positively charged), electrostatic forces can be generated that urge the first nanoparticle 12A and the second nanoparticle 12B into a second position that is shown in FIG. 1B. In this second position, the first cantilever member 14A and the second cantilever member 14B are bent or deflected towards one another, and the first nanoparticle 12A and the second nanoparticle 12B are separated by a second distance $D_2$ that is less than the distance $D_1$ shown in FIG. 1A.

If the first nanoparticle 12A and the second nanoparticle 12B are electrically charged with like charge (i.e., the first nanoparticle 12A and the second nanoparticle 12B are both charged with either positive charge or negative charge), electrostatic forces can be generated that urge the first nanoparticle 12A and the second nanoparticle 12B into a third position shown in FIG. 1C. In this third position, the first cantilever member 14A and the second cantilever member 14B are bent or deflected away from one another, and the first nanoparticle 12A and the second nanoparticle 12B are separated by a third distance $D_3$ that is greater than the distance $D_1$ shown in FIG. 1A.

The NERS-active structure 10 shown in FIGS. 1A-1C can be used to perform NERS on an analyte. The analyte can be provided between or proximate to the first nanoparticle 12A and the second nanoparticle 12B. The spacing D between the first nanoparticle 12A and the second nanoparticle 12B can then be varied between $D_1$ shown in FIG. 1A, $D_2$ shown in FIG. 1B, and $D_3$ shown in FIG. 1C by electrically charging the first nanoparticle 12A and the second nanoparticle 12B. The spacing can be varied while irradiating the analyte and the NERS-active structure 10 to perform NERS. The spacing between the first nanoparticle 12A and the second nanoparticle 12B at which the intensity of observed Raman scattered radiation is maximized can be identified and maintained.

Alternatively, the first nanoparticle 12A and the second nanoparticle 12B can be made to oscillate between the second position shown in FIG. 1B and the third position shown in FIG. 1C while performing NERS. For example, one of the first region 17A and the second region 17B can be electrically grounded and a pulsed electrical signal may be applied to the other region. The pulsed electrical signal may be, for example, sinusoidal, square, or triangular. The characteristics of the electrical signal such as, for example, amplitude and frequency, can then be adjusted to optimize the intensity of the Raman scattered radiation. By oscillating the position of the first nanoparticle 12A and the second nanoparticle 12B, a range of distances D may be provided, some of which may substantially enhance the intensity of Raman scattered radiation.

In this manner, the NERS-active structure 10 can be used to selectively vary the distance between the first nanoparticle 12A and the second nanoparticle 12B while performing NERS.

Figure 2:
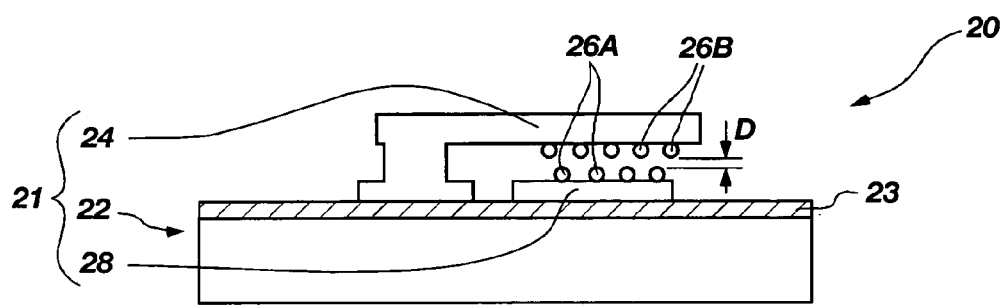
FIG. 2 is a side view of an exemplary NERS-active structure that embodies teachings of the present invention and that includes nanoparticles disposed on a cantilever member.

Another exemplary NERS-active structure 20 that embodies teachings of the present invention is shown in FIG. 2. The NERS-active structure 20 includes a substrate 22, an electrically insulating layer 23, an electrically conductive, laterally extending, elongated cantilever member 24, a first plurality of nanoparticles 26A, and a second plurality of nanoparticles 26B. The first plurality of nanoparticles 26A is disposed on an electrically conductive nanoparticle platform member 28. The second plurality of nanoparticles 26B is disposed on the unsupported end of cantilever member 24 proximate to the first plurality of nanoparticles 26A and separated therefrom by a distance D. The cantilever member 24 is electrically isolated from the nanoparticle platform member 28 by the insulating layer 23 on the substrate 22.

The substrate 22 can be formed from, for example, a crystalline or polycrystalline silicon wafer. The first plurality of nanoparticles 26A and the second plurality of nanoparticles 26B are formed from a NERS-active material. The nanoparticle platform member 28 and the cantilever member 24 can be formed from, for example, a metal or semiconductive material such as silicon, germanium, doped silicon or doped germanium.

Electrodes (not shown) may be provided on the NERS-active structure 20 for applying a voltage between the cantilever member 24 and the nanoparticle platform member 28.

In this configuration, an active nanoparticle support structure 21 for supporting the first plurality of nanoparticles 26A and the second plurality of nanoparticles 26B is provided by substrate 22, cantilever member 24, and nanoparticle platform member 28.

The NERS-active structure 20 will assume the position shown in FIG. 2 when the cantilever member 24 and the nanoparticle platform member 28 are not significantly electrically charged. If the cantilever member 24 and the nanoparticle platform member 28 are electrically charged with opposite charge (i.e., either the cantilever member 24 or the nanoparticle platform member 28 is negatively charged and the other positively charged), electrostatic forces can be generated that cause the cantilever member 24 to deflect downward towards the nanoparticle platform member 28 and the distance between the first plurality of nanoparticles 26A and the second plurality of nanoparticles 26B to decrease.

If the cantilever member 24 and the nanoparticle platform member 28 are electrically charged with like charge (i.e., the cantilever member 24 and the nanoparticle platform member 28 are both charged with either positive charge or negative charge), electrostatic forces can be generated that cause the cantilever member 24 to deflect upward away from the nanoparticle platform member 28 and the distance between the first plurality of nanoparticles 26A and the second plurality of nanoparticles 26B to increase.

The NERS-active structure 20 shown in FIG. 2 can be used to perform NERS on an analyte. The analyte can be provided between or proximate to the first plurality of nanoparticles 26A and the second plurality of nanoparticles 26B. The spacing D between the first plurality of nanoparticles 26A and the second plurality of nanoparticles 26B can then be varied by electrically charging the cantilever member 24 and nanoparticle platform member 28 while irradiating the analyte and the NERS-active structure 20. The spacing can be varied while performing NERS. The spacing D between the first plurality of nanoparticles 26A and the second plurality of nanoparticles 26B at which the intensity of observed Raman scattered radiation is maximized can be identified and maintained.

Alternatively, the position of the end of the cantilever member 24 supporting the second plurality of nanoparticles 26B can be made to oscillate up and down while performing NERS. For example, the nanoparticle platform 28 can be electrically grounded and a pulsed electrical signal may be applied to the cantilever member 24. The pulsed electrical signal may be, for example, sinusoidal, square, or triangular. The characteristics of the electrical signal such as, for example, amplitude and frequency can then be adjusted to optimize the intensity of the Raman scattered radiation. By oscillating the position of the end of the cantilever member 24, a range of distances D between the first plurality of nanoparticles 26A and the second plurality of nanoparticles 26B can be provided, some of which may substantially enhance the intensity of Raman scattered radiation.

In this manner, the NERS-active structure 20 can be used to selectively vary the distance between the first plurality of nanoparticles 26A and the second plurality of nanoparticles 26B while performing NERS.

Figure 3:
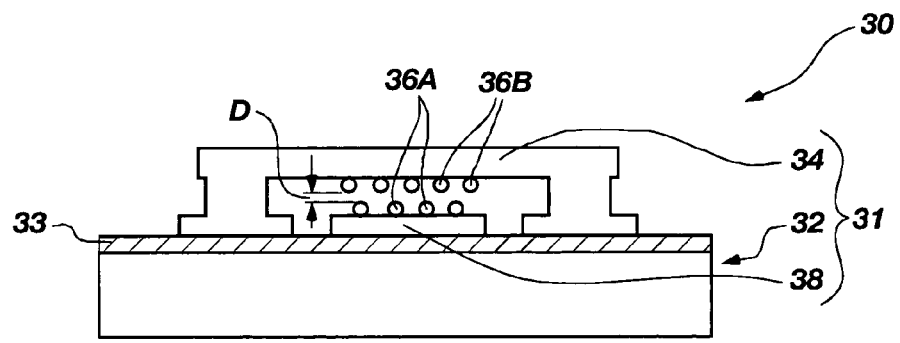
FIG. 3 is a side view of an exemplary NERS-active structure that embodies teachings of the present invention and that includes nanoparticles disposed on a deflectable bridge-type beam member.

Another exemplary NERS-active structure 30 that embodies teachings of the present invention is shown in FIG. 3. The NERS-active structure 30 includes a substrate 32, an electrically insulating layer 33, an electrically conductive deflectable bridge-type beam 34, a first plurality of nanoparticles 36A, and a second plurality of nanoparticles 36B. The first plurality of nanoparticles 36A are disposed on an electrically conductive nanoparticle platform member 38. The second plurality of nanoparticles 36B are disposed on the deflectable bridge-type beam 34 near the center thereof proximate to the first plurality of nanoparticles 36A. The second plurality of nanoparticles 36B are separated from the first plurality of nanoparticles 36A by a distance D. The bridge-type beam 34 is electrically isolated from the nanoparticle platform member 38 by the insulating layer 33 on the substrate 32.

The substrate 32 can be formed from, for example, a crystalline or polycrystalline silicon wafer. The first plurality of nanoparticles 36A and the second plurality of nanoparticles 36B are formed from a NERS-active material. The nanoparticle platform member 38 and the bridge-type beam 34 may include, for example, a semiconductor material, such as doped silicon or doped germanium.

In this configuration, an active nanoparticle support structure 31 for supporting the first plurality of nanoparticles 36A and the second plurality of nanoparticles 36B is provided by the substrate 32, the bridge-type beam 34, and the nanoparticle platform member 38.

The NERS-active structure 30 will assume the position shown in FIG. 3 when the bridge-type beam 34 and the nanoparticle platform member 38 are not significantly electrically charged. If the bridge-type beam 34 and the nanoparticle platform member 38 are electrically charged with opposite charge (i.e., either the bridge-type beam 34 or the nanoparticle platform member 38 is negatively charged and the other positively charged), electrostatic forces can be generated that cause the center of the bridge-type beam 34 to deflect downward towards the nanoparticle platform member 38 and the distance between the first plurality of nanoparticles 36A and the second plurality of nanoparticles 36B to decrease.

If the bridge-type beam 34 and the nanoparticle platform member 38 are electrically charged with like charge (i.e., the bridge-type beam 34 and the nanoparticle platform member 38 are both charged with either positive charge or negative charge), electrostatic forces can be generated that cause the center of the bridge-type beam 34 to deflect upward away from the nanoparticle support member 38 and the distance between the first plurality of nanoparticles 36A and the second plurality of nanoparticles 36B to increase.

The NERS-active structure 30 shown in FIG. 3 can be used to perform NERS on an analyte. The analyte can be provided between or proximate to the first plurality of nanoparticles 36A and the second plurality of nanoparticles 36B. The spacing D between the first plurality of nanoparticles 36A and the second plurality of nanoparticles 36B can be varied by charging the bridge-type beam 34 and the nanoparticle platform member 38 while irradiating the analyte and the NERS-active structure 30. The spacing can be varied while performing NERS. The spacing D between the first plurality of nanoparticles 36A and the second plurality of nanoparticles 36B at which the intensity of observed Raman scattered radiation is maximized can be identified and maintained.

Alternatively, the center of the bridge-type beam 34 can be made to oscillate up and down while performing NERS on the analyte. By oscillating the center of the bridge-type beam 34, a range of distances D between the first plurality of nanoparticles 36A and the second plurality of nanoparticles 36B can be provided, some of which might substantially enhance the intensity of Raman scattered radiation. For example, the nanoparticle platform member 38 can be electrically grounded and a pulsed electrical signal can be applied to the bridge-type beam 34. The pulsed electrical signal can be, for example, sinusoidal, square, or triangular. The characteristics of the electrical signal, such as, for example, amplitude and frequency, can then be adjusted to optimize the intensity of the Raman scattered radiation.

In this manner, the NERS-active structure 30 can be used to selectively vary the distance between the first plurality of nanoparticles 36A and the second plurality of nanoparticles 36B while performing NERS.

Figure 4A:
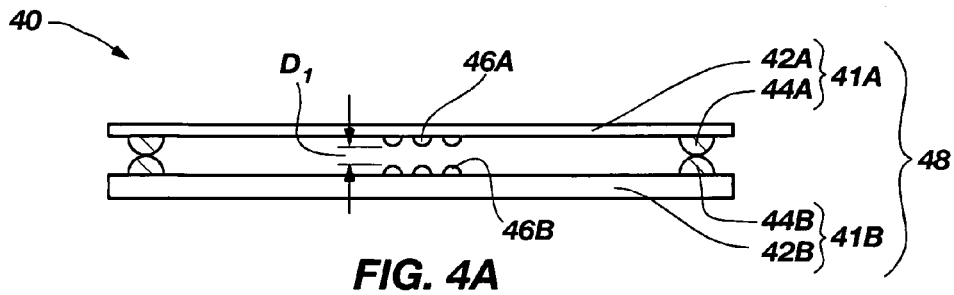
FIG. 4A is a side view of an exemplary NERS-active structure that embodies teachings of the present invention and that includes nanoparticles disposed on a deflectable plate-shaped member.
Figure 4B:
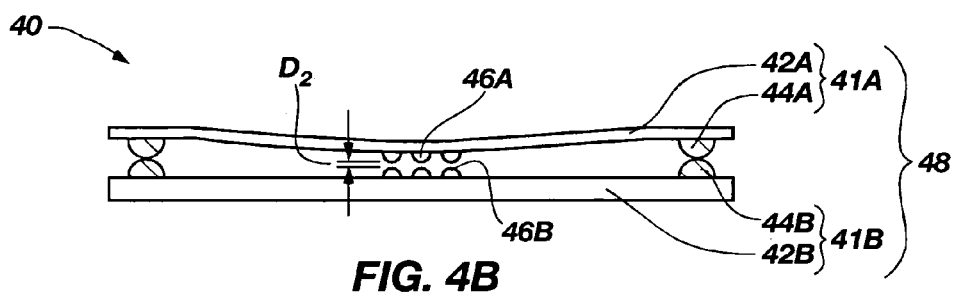
FIG. 4B is a side view of the exemplary NERS-active structure shown in FIG. 4A showing the plate-shaped member in a deflected position.
Figure 4C:
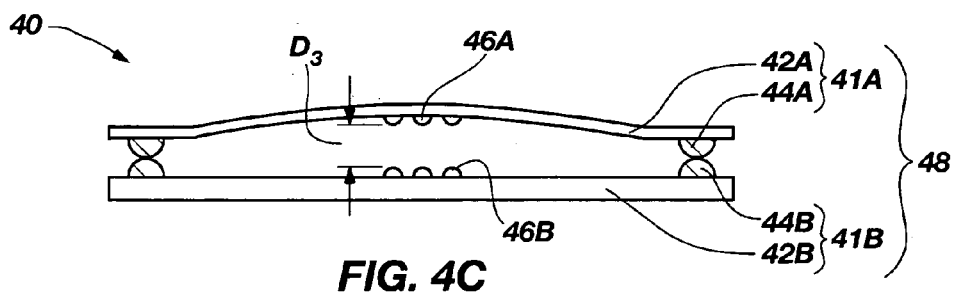
FIG. 4C is a side view of the exemplary NERS-active structure shown in FIG. 4A showing the plate-shaped member in another deflected position.
Figure 5:
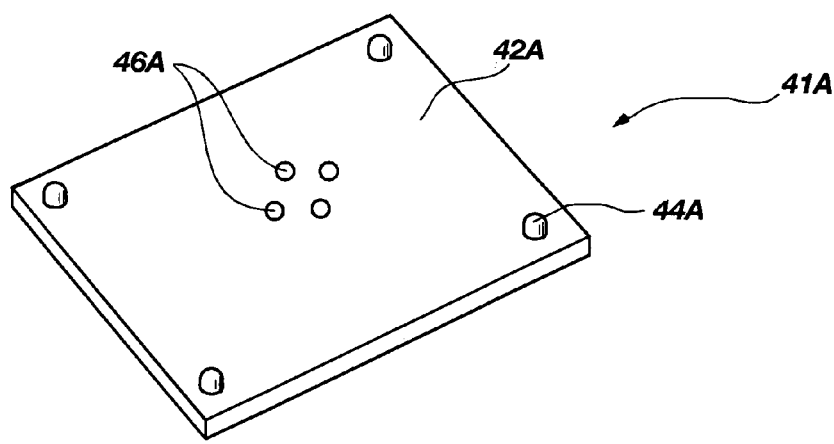
FIG. 5 is a perspective view of a plate-shaped member shown in FIGS. 4A-4C.

Another exemplary NERS-active structure 40 that embodies teachings of the present invention is shown in FIGS. 4A-4C. The NERS-active structure 40 can be formed from a first plate-shaped member 41A and a second plate-shaped member 41B. FIG. 5 is a perspective view of the first plate-shaped member 41A. The first plate-shaped member 41A includes a substrate 42A and four electrically insulating spacers 44A. A plurality of nanoparticles 46A formed from a NERS-active material is disposed on the substrate 42A near the center thereof. The second plate-shaped member 41B shown in FIGS. 4A-4C is substantially similar to the first plate-shaped member 41A shown in FIG. 5 and includes a substrate 42B and four electrically insulating spacers 44B. A plurality of nanoparticles 46B formed from a NERS-active material is disposed on the substrate 42B near the center thereof. The substrate 42A of the first plate-shaped member 41A can optionally be thinner than the substrate 42B of the second plate-shaped member 41B to more easily allow the center of the substrate 42A to be deflected relative to the substrate 42B.

The substrate 42A and the substrate 42B can be formed from any material capable of conducting electrical charge such as, for example, a doped crystalline or polycrystalline silicon wafer. The electrically insulating spacers 44A and the electrically insulating spacers 44B can be formed from, for example, silicon oxide. The plurality of nanoparticles 46A and the plurality of nanoparticles 46B are formed from a NERS-active material.

The NERS-active structure 40 can be formed by stacking the first plate-shaped member 41A on top of the second plate-shaped member 41B such that the insulating spacers 44A abut against the insulating spacers 44B. In this configuration, the plurality of nanoparticles 46A are disposed proximate to the plurality of nanoparticles 46B and separated therefrom by a distance. The substrate 42A is electrically isolated from the substrate 42B by the insulating spacers 44A and the insulating spacers 44B. Alternatively, substrate 42A can be electrically isolated from the substrate 42B by one set of insulating spacers (i.e., either 44A or 44B) so long as sufficient spacing is provided between substrate 42A and substrate 42B. Electrodes (not shown) can be formed on the substrate 42A and the substrate 42B for electrically charging the substrate 42A and the substrate 42B. In this configuration, an active nanoparticle support structure 48 for supporting the plurality of nanoparticles 46A and the plurality of nanoparticles 46B is provided by the first plate-shaped member 41A and the second plate-shaped member 41B.

The NERS-active structure 40 shown in FIGS. 4A-4C will assume a first position shown in FIG. 4A when the substrate 42A and the substrate 42B are not significantly electrically charged. In this first position, the substrate 42A is substantially flat or planar, and the plurality of nanoparticles 46A is separated from the plurality of nanoparticles 46B by a first distance $D_1$.

If the substrate 42A and the substrate 42B are electrically charged with opposite charge (i.e., either the substrate 42A or the substrate 42B is negatively charged and the other positively charged), electrostatic forces can be generated that cause the center of the substrate 42A to deflect downward towards the substrate 42B to a second position shown in FIG. 4B. In this second position, the plurality of nanoparticles 46A is separated from the plurality of nanoparticles 46B by a second distance $D_2$ that is less than the first distance $D_1$ shown in FIG. 4A.

If the substrate 42A and the substrate 42B are electrically charged with like charge (i.e., the substrate 42A and the substrate 42B are both charged with either positive charge or negative charge), electrostatic forces can be generated that cause the center of the substrate 42A to deflect upward away from the substrate 42B to a third position shown in FIG. 4C. In this third position, the plurality of nanoparticles 46A is separated from the plurality of nanoparticles 46B by a third distance $D_3$ that is greater than the first distance $D_1$ shown in FIG. 4A The NERS-active structure 40 shown in FIGS. 4A-4C can be used to perform NERS on an analyte. The analyte can be provided between the plurality of nanoparticles 46A and the plurality of nanoparticles 46B. The spacing between the plurality of nanoparticles 46A and the plurality of nanoparticles 46B can then be varied by electrically charging the substrate 42A and the substrate 42B while irradiating the analyte and the NERS-active structure 40. The spacing can be varied while performing NERS. The spacing between the plurality of nanoparticles 46A and the plurality of nanoparticles 46B at which the intensity of observed Raman scattered radiation is a maximum can be identified and maintained.

Alternatively, the center of the substrate 42A can be made to oscillate up and down between the second position shown in FIG. 4B and the third position shown in FIG. 4C while performing NERS. By oscillating the center of the substrate 42A, a range of distances between the plurality of nanoparticles 46A and the plurality of nanoparticles 46B can be provided, some of which might substantially enhance the intensity of Raman scattered radiation. For example, the substrate 42B can be electrically grounded and a pulsed electrical signal can be applied to the substrate 42A. The pulsed electrical signal can be, for example, sinusoidal, square, or triangular. The characteristics of the electrical signal, such as, for example, amplitude and frequency, can then be adjusted to optimize the intensity of the Raman scattered radiation. In this manner, the NERS-active structure 40 can be used to selectively vary the distance between the first plurality of nanoparticles 46A and the second plurality of nanoparticles 46B.

Figure 6A:
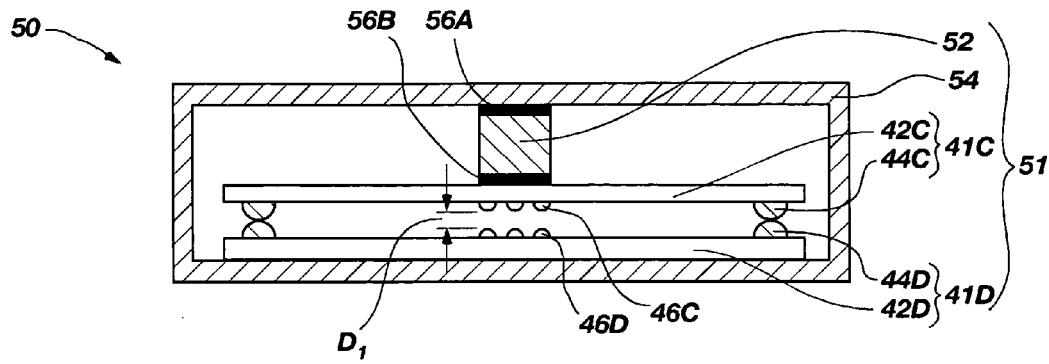
FIG. 6A is a side view of an exemplary NERS-active structure that embodies teachings of the present invention and that includes nanoparticles disposed on a deflectable plate-shaped member and a piezoelectric device.
Figure 6B:
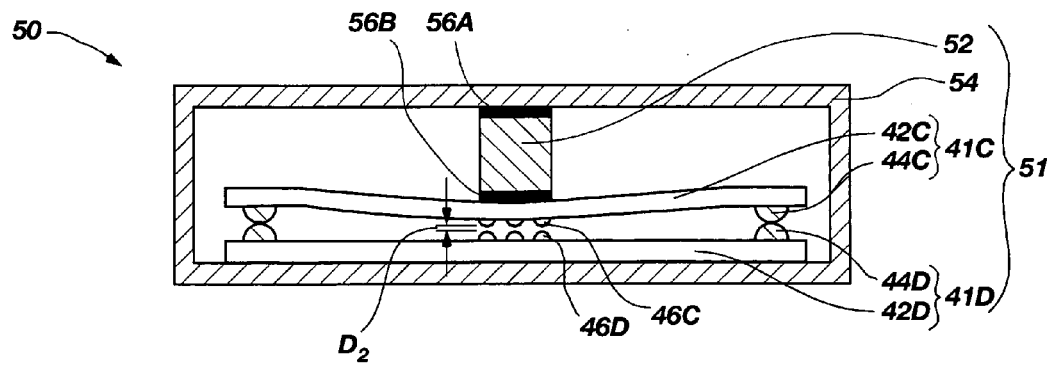
FIG. 6B is a side view of the exemplary NERS-active structure shown in FIG. 6A showing the plate-shaped member in a deflected position.

Another exemplary NERS-active structure 50 that embodies teachings of the present invention is shown in FIGS. 6A-6B. The NERS-active structure 50 includes a structure similar to the NERS-active structure 40 shown in FIGS. 4A-4C and includes a first plate-shaped member 41C stacked against a second plate shaped member 41D. Mechanical forces are used to deflect the center of the first plate-shaped member 41C relative to the second plate-shaped member 41D, in contrast to the use of electrostatic forces, as previously discussed in relation to the NERS-active structure 40 of FIGS. 4A-4C.

The first plate-shaped member 41C includes a substrate 42C and four electrically insulating spacers 44C. A plurality of nanoparticles 46C formed from a NERS-active material is disposed on the substrate 42C near the center thereof. The second plate-shaped member 41D also includes a substrate 42D and four electrically insulating spacers 44D. A plurality of nanoparticles 46D formed from a NERS-active material is disposed on the substrate 42D near the center thereof. The substrate 42C of the first plate-shaped member 41C can optionally be thinner than the substrate 42D of the second plate-shaped member 41D to allow the center of the substrate 42C to be deflected relative to the substrate 42D.

The mechanical forces used to deflect the center of the first plate-shaped member 41C can be generated by, for example, a piezoelectric device 52. The piezoelectric device 52 can be disposed between a surface of the substrate 42C and a retaining structure 54. The piezoelectric device 52 can be formed from any piezoelectric material such as, for example, lead zirconate titanate (PZT), barium titanate, or quartz. A first electrode 56A and a second electrode 56B can be provided on opposite ends of the piezoelectric device 52 for applying a voltage across the piezoelectric material.

In this configuration, an active nanoparticle support structure 51 for supporting the plurality of nanoparticles 46C and the plurality of nanoparticles 46D is provided by the first plate-shaped member 41C, the second plate-shaped member 41D, the piezoelectric device 52, and the retaining structure 54.

In the absence of a voltage between the first electrode 56A and the second electrode 56B, the substrate 42C assumes a generally flat planar first configuration shown in FIG. 6A. In this first configuration, the plurality of nanoparticles 46C is separated from the plurality of nanoparticles 46D by a first distance $D_1$. Applying a voltage across the piezoelectric material causes the physical dimensions of the piezoelectric device 52 to change. As the physical dimensions of the piezoelectric device 52 change, the piezoelectric device 52 will exert a force against both the retaining structure 54 and the substrate 42C, which causes the center of the substrate 42C to deflect relative to the substrate 42C.

Applying a voltage of a first polarity across the piezoelectric material can cause the piezoelectric device 52 to expand in the direction perpendicular to the plane of the substrate 42C. This causes the piezoelectric device 52 to exert a force against both the retaining structure 54 and the substrate 42C, which causes the center of the substrate 42C to deflect downward towards the substrate 42D to a second position shown in FIG. 6B. In this second position, the plurality of nanoparticles 46C is separated from the plurality of nanoparticles 46D by a second distance $D_2$ that is less than the first distance $D_1$ shown in FIG. 6A.

If the polarity of the voltage applied across the piezoelectric material is reversed the piezoelectric device 52 will contract in the direction perpendicular to the plane of the substrate 42C. This may cause the piezoelectric device 52 to exert a force against both the retaining structure 54 and the substrate 42C, which may cause the center of the substrate 42C to deflect upwards away from the substrate 42D to a third position (not shown). In this third position, the plurality of nanoparticles 46C is separated from the plurality of nanoparticles 46D by a third distance that is greater than the first distance $D_1$ shown in FIG. 6A.

Alternatively, other means for applying a mechanical force to the substrate 42C to deflect the center portion of the substrate 42C relative to the substrate 42D could be employed. These other means might include, for example, pneumatic, hydraulic, or other electro-mechanical means.

The NERS-active structure 50 shown in FIGS. 6A-6B can be used to perform NERS on an analyte. The analyte can be provided between or proximate to the plurality of nanoparticles 46C and the plurality of nanoparticles 46D. The spacing between the plurality of nanoparticles 46C and the plurality of nanoparticles 46D can then be varied by applying a voltage across the piezoelectric device 52, which causes the center of the substrate 42C to deflect downward towards the substrate 42D. The spacing can be varied while performing NERS. The spacing between the plurality of nanoparticles 46C and the plurality of nanoparticles 46D at which the intensity of observed Raman scattered radiation is maximized can be identified and maintained.

Alternatively, the center of the substrate 42C could be made to oscillate up and down while performing NERS. By oscillating the center of the substrate 42C, a range of distances between the plurality of nanoparticles 46C and the plurality of nanoparticles 46D can be provided, some of which may substantially enhance the intensity of Raman scattered radiation. For example, a pulsed electrical signal may be applied to the piezoelectric device 52 while performing NERS. The pulsed electrical signal may be, for example, sinusoidal, square, or triangular. The characteristics of the electrical signal such as, for example, amplitude and frequency can then be adjusted to optimize the intensity of the Raman scattered radiation.

In this manner, the NERS-active structure 50 can be used to selectively vary the distance between the first plurality of nanoparticles 46C and the second plurality of nanoparticles 46D.

Figure 7A:
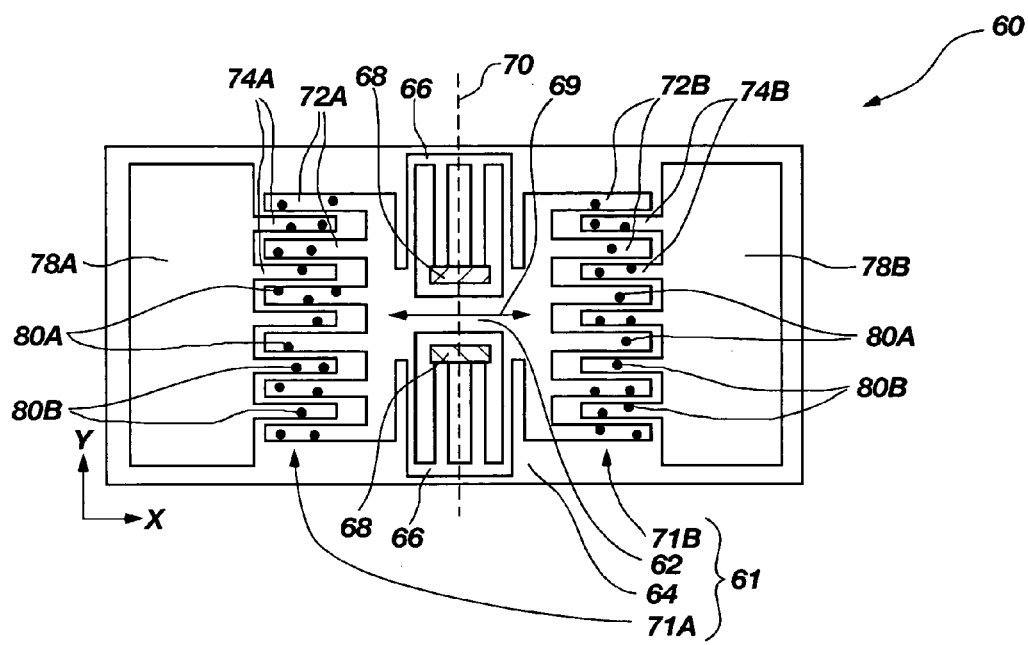
FIG. 7A is a top plan view of an exemplary NERS-active structure that embodies teachings of the present invention and that includes nanoparticles disposed on a moveable base member that is attached to a static base member.
Figure 7B:
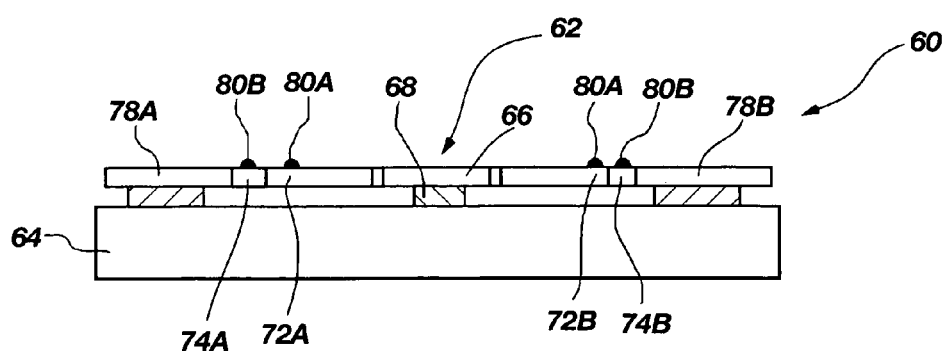
FIG. 7B is a side view of the exemplary NERS-active structure shown in FIG. 7A.

Another exemplary NERS-active structure 60 that embodies teachings of the present invention is shown in FIGS. 7A-7B. The NERS-active structure 60 includes a movable base member 62 attached to a static base member 64. The movable base member 62 is configured to move or oscillate laterally in either direction relative to the static base member 64.

The movable base member 62 is attached to and supported above the static base member 64 by way of two mechanical spring members 66 and two anchor members 68. The anchor members 68 are attached to the static base member 64. The mechanical spring members 66 extend between the anchor members 68 and the movable base member 62. The mechanical spring members 66 can be mechanically deformed to allow the moveable base member 62 to move laterally to either side in the directions indicated by double-ended arrow 69 relative to the static base member 64.

The NERS-active structure 60 can be symmetric about a dividing line 70. The NERS-active structure 60 also can include a first inter-digital structure 71A and a second inter-digital structure 71B. The inter-digital structure 71A includes a first plurality of generally aligned digit members 72A that are attached to and extend from the movable base member 62, and a second plurality of generally aligned digit members 74A that are attached to and extend from a first electrode 78A. The first electrode 78A is attached to the static base member 64. Each digit member of the first plurality of generally aligned digit members 72A is disposed in the spaces between the digit members of the second plurality of generally aligned digit members 74A. Similarly, the second inter-digital structure 71B includes a second plurality of generally aligned digit members 72B that are attached to and extend from the movable base member 62, and a second plurality of generally aligned digit members 74B that are attached to and extend from a second electrode 78B. The second electrode 78B is attached to the static base member 64. Each digit member of the first plurality of generally aligned digit members 72B is disposed in the spaces between the digit members of the second plurality of generally aligned digit members 74B.

A first plurality of nanoparticles 80A formed from a NERS-active material is disposed on the plurality of generally aligned digit members 72A and 72B that extend from the movable base member 62. A second plurality of nanoparticles 80B formed from a NERS-active material is disposed on the generally aligned digit members 74A and 74B that are attached to the electrodes 78A and 78B.

FIG. 7B is a side view of the NERS-active structure 60 illustrated in FIG. 7A. As seen therein, the movable base member 62 is supported above the static base member 64 by the mechanical spring members 66, which are attached to the anchor members 68.

The static base member 62 can be formed from, for example, a polycrystalline silicon wafer. The electrodes 78A and 78B, the movable base member 62, and the spring members 66 can be formed from any material capable of conducting electrical charge such as, for example, doped polycrystalline silicon. The anchor members 68 should be electrically insulating and can be formed from, for example, silicon oxide. The plurality of nanoparticles 80A and the plurality of nanoparticles 80B are formed from a NERS-active material.

In this configuration, an active nanoparticle support structure 61 for supporting the plurality of nanoparticles 80A and the plurality of nanoparticles 80B is provided by the static base member 64, the moveable base member 62, the first inter-digital structure 71A and the second inter-digital structure 71B.

An electric signal can be applied to one or both of the electrodes 78A and 78B to generate electrostatic forces between the plurality of generally aligned digit members 72A, 72B extending from the movable base member 62 and the plurality of generally aligned digit members 74A, 74B that are attached to electrodes 78A and 78B and fixed to the static base member 64. These electrostatic forces may cause the spring members 66 to bend and the movable base member 62 to move laterally in the X direction relative to the static base member 64 in the directions shown by double-ended arrow 69. Movement of the movable base member 62 relative to the static base member 64 in the X direction causes the distance between the first plurality of nanoparticles 80A and the second plurality of nanoparticles 80B to change.

The NERS-active structure 60 shown in FIGS. 7A-7B can be used to perform NERS on an analyte. The analyte can be provided between or proximate to the first plurality of nanoparticles 80A and the second plurality of nanoparticles 80B. The spacing between the first plurality of nanoparticles 80A and the second plurality of nanoparticles 80B then can be varied by electrically charging one or both of the electrodes 78A and 78B (both electrodes should be charged with other than equal charges of the same polarity) while irradiating the analyte and the NERS-active structure 60. The spacing can be varied while performing NERS. The spacing between the first plurality of nanoparticles 80A and the second plurality of nanoparticles 80B at which the intensity of observed Raman scattered radiation is a maximum can be identified and maintained.

Alternatively, the movable base member 62 could be made to oscillate back and forth between the electrodes 78A and 78B while performing NERS. For example, one electrode 78A, 78B can be electrically grounded and a pulsed electrical signal can be applied to the other electrode 78A, 78B. The pulsed electrical signal may be, for example, sinusoidal, square, or triangular. The characteristics of the electrical signal such as, for example, amplitude and frequency can then be adjusted to optimize the intensity of the Raman scattered radiation. By oscillating the movable base member 62, a range of distances between the first plurality of nanoparticles 80A and the second plurality of nanoparticles 80B can be provided, some of which may substantially enhance the intensity of Raman scattered radiation.

Alternatively, a first pulsed electrical signal can be applied to one electrode (e.g., 78A) and a second pulsed electrical signal of equal frequency can be applied to the other electrode (e.g., 78B) the second pulsed electrical signal being out of phase with the first pulsed electrical signal. The phase of the second pulsed electrical signal can be shifted 180° relative to the phase of the first pulsed electrical signal.

In addition, the frequency of the electrical signal applied to one or both of the electrodes 78A and 78B can be adjusted to match the natural mechanical oscillating frequency of the movable base member 64 (which is at least partially a function of the mass of the movable base member 62 and the spring constant of the mechanical spring members 66). Matching the frequency of the electrical signal to the natural mechanical oscillating frequency of the movable base member 64 may increase the amplitude of the oscillations of the movable base member 64.

In an alternative configuration, each electrode 78A, 78B could be movably attached to the static base member 64 in a manner that allows each electrode 78A, 78B to move in the Y direction (perpendicular to the direction of movement of the movable base member 62). In this configuration, the second plurality of nanoparticles 80B that is disposed on the generally aligned digit members 74A and 74B that are attached to the electrodes 78A and 78B can be moved in the Y direction, which provides a greater range of possible movements that can be made between the first plurality of nanoparticles 80A and the second plurality of nanoparticles 80B. In this manner, the NERS-active structure 60 can be used to selectively vary the distance between the plurality of nanoparticles 80A and the plurality of nanoparticles 80B.

In addition to the NERS-active structure 60 shown in FIGS. 7A-7B, each of the NERS-active structures shown in FIGS. 2, 3, 4A-4C, and 6A-6C includes a static base member and a movable base member, a first nanoparticle being disposed on the static base member and a second nanoparticle being disposed on the movable base member. Cantilever members, deflectable bridge-type beam members, and deflectable plate-shaped members all are considered to be movable base members that can be used to support nanoparticles in a moveable position relative to nanoparticles disposed on a static base member, such as a substrate. NERS-active structures that include nanoparticles formed from a NERS-active material can be provided wherein the distance or spacing between the nanoparticles is selectively variable while performing NERS by providing the nanoparticles on an elastically deformable substrate.

A representative NERS-active structure 90 that embodies teachings of the present invention is shown in FIGS. 8A-8D. The NERS-active structure 90 includes an elastically deformable dielectric substrate 92 and a plurality of nanoparticles 94 formed from a NERS-active material. The elastically deformable dielectric substrate 92 can be formed from, for example, a polymer material. Each nanoparticle 94 is attached to a surface of the elastically deformable dielectric substrate 92 such that elastic deformation of the dielectric substrate causes the distance between the nanoparticles 94 to change. In this configuration, an active nanoparticle support structure for supporting the plurality of nanoparticles 94 is provided by the elastically deformable dielectric substrate 92.

Figure 8A:
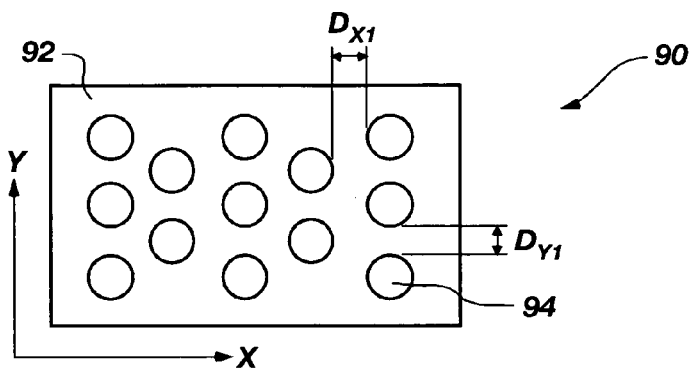
FIG. 8A is a top plan view of an exemplary NERS-active structure that embodies teachings of the present invention and that includes nanoparticles disposed on a deformable substrate.
Figure 8B:
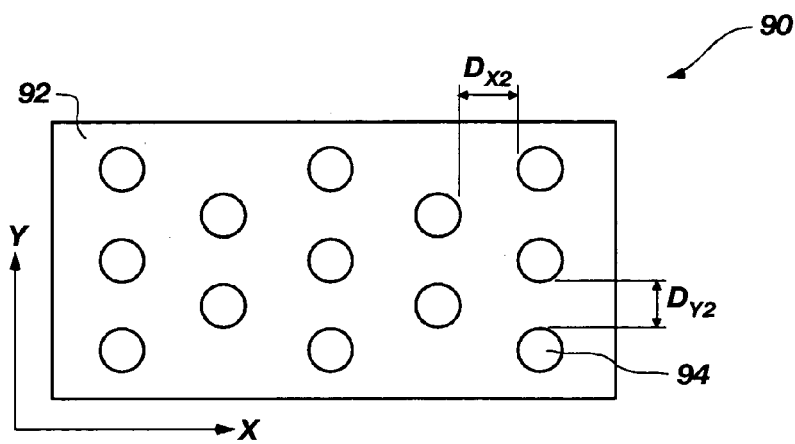
FIG. 8B is a top plan view of the exemplary NERS-active structure shown in FIG. 8A illustrating the deformable substrate in a deformed state.

The plurality of nanoparticles 94 can be arranged in an ordered array, as illustrated in FIGS. 8A-8B. Each nanoparticle 94 is separated from adjacent nanoparticles 94 in the X direction by a distance $D_{X1}$ and in a Y direction by a distance $D_{Y1}$ when the dielectric substrate 92 is in a non-deformed state, as shown in FIG. 8A. The dielectric substrate 92 can be elastically stretched or compressed in the X direction, the Y direction, or in both the X and Y directions. If the dielectric substrate is elastically stretched in both the X and Y directions to a deformed state illustrated in FIG. 8B, each nanoparticle 94 is separated from adjacent nanoparticles 94 in the X direction by a distance $D_{X2}$ and in a Y direction by a distance $D_{Y2}$. The distance $D_{X2}$ shown in FIG. 8B is greater than the distance $D_{X1}$ shown in FIG. 8A, and the distance $D_{Y2}$ shown in FIG. 8B is greater than the distance $D_{Y1}$ shown in FIG. 8A.

Alternatively, the dielectric substrate 92 shown in FIG. 8A could be elastically compressed in the X direction, the Y direction, or in both the X and Y directions to decrease the distances $D_{X1}$ and $D_{Y1}$ separating adjacent nanoparticles 94 in the ordered array.

Figure 8C:
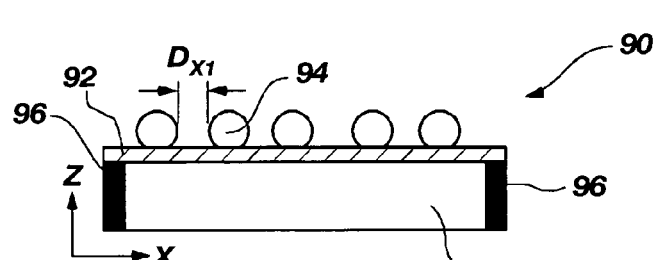
FIG. 8C is a side view of the exemplary NERS-active structure shown in FIGS. 8A-8B illustrating the deformable substrate attached to the surface of a piezoelectric device.

The dielectric substrate 92 shown in FIGS. 8A-8B can be stretched or compressed in many ways. For example, the elastically deformable dielectric substrate 92 can be attached to the surface of a piezoelectric device 95 as shown in FIG. 8C such that each nanoparticle 94 is disposed in a fixed position relative to a point on the surface of the piezoelectric device 95. Electrodes 96 are provided on two opposite sides of the piezoelectric device 95 that can be used to apply a voltage across the piezoelectric material. The piezoelectric device 95 can be formed from any known piezoelectric material.

Figure 8D:
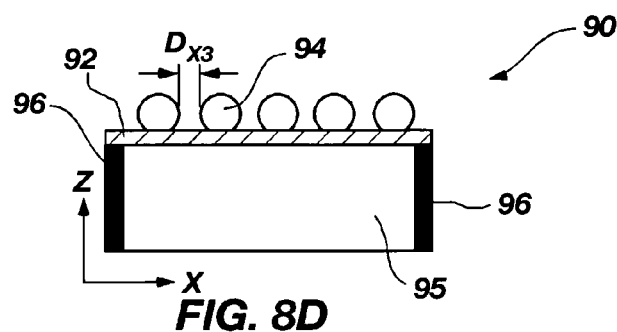
FIG. 8D is a side view of the exemplary NERS-active structure shown in FIG. 8C illustrating the piezoelectric device and the deformable substrate in a deformed state.

Applying a voltage across the piezoelectric material may change the physical dimensions of the piezoelectric device 95. FIG. 8D illustrates the NERS-active structure 90 while a voltage is applied between the electrodes 96. As seen therein, the piezoelectric device 95 and the dielectric substrate 92 disposed on the surface thereof are compressed in the X direction. Compressing the dielectric substrate 92 causes the distance separating adjacent nanoparticles 94 in the X direction to decrease to a distance $D_{X3}$, which is shorter than the distance $D_{X1}$ shown in FIG. 8C.

The NERS-active structure 90 shown in FIGS. 8A-8D can be used to perform NERS on an analyte. The analyte can be provided between or proximate to adjacent nanoparticles 94. The spacing between the nanoparticles 94 then can be varied by elastically deforming the dielectric substrate 92 while irradiating the analyte and the NERS-active structure 90. The spacing can be varied while performing NERS. The spacing between the nanoparticles 94 at which the intensity of observed Raman scattered radiation is a maximum can be identified and maintained.

If the NERS-active structure 90 is disposed on a piezoelectric device as shown in FIGS. 8C-8D, the elastically deformable substrate 92 could be made to oscillate back and forth between an elastically deformed state and a non-deformed state while performing NERS. For example, one electrode 96 can be electrically grounded and a pulsed electrical signal can be applied to the other electrode 96. The pulsed electrical signal may be, for example, sinusoidal, square, or triangular. The characteristics of the electrical signal, such as, for example, amplitude and frequency, can then be adjusted to optimize the intensity of the Raman scattered radiation. By oscillating the elastic deformation of the dielectric substrate 92, a range of distances between the nanoparticles 94 can be provided, some of which may substantially enhance the intensity of Raman scattered radiation. In this manner, the NERS-active structure 90 can be used to selectively vary the distance between adjacent nanoparticles in the plurality of nanoparticles 94.

While the number and size of the nanoparticles 94 disposed on the dielectric substrate 92 shown in FIGS. 8A-8D imply that the size of the dielectric substrate is small, the figures are not actual views of any particular NERS-active structure, but are merely idealized representations which are employed to describe the present invention. In actuality, the dielectric substrate 92 can be much larger than the nanoparticles 94. For example, the dielectric substrate 92 can be a polymeric tape having millimeter sized dimensions. In such a configuration, the polymeric tape can be stretched or compressed using simple mechanical or electromechanical means.

Figure 9A:
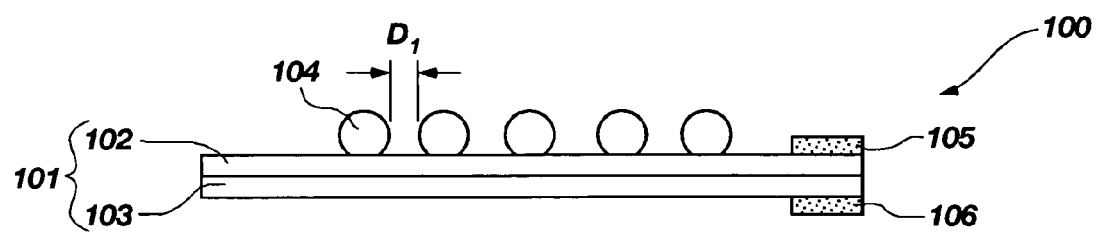
FIG. 9A is a side view of an exemplary NERS-active structure that embodies teachings of the present invention and that includes nanoparticles disposed on a deformable substrate.
Figure 9B:
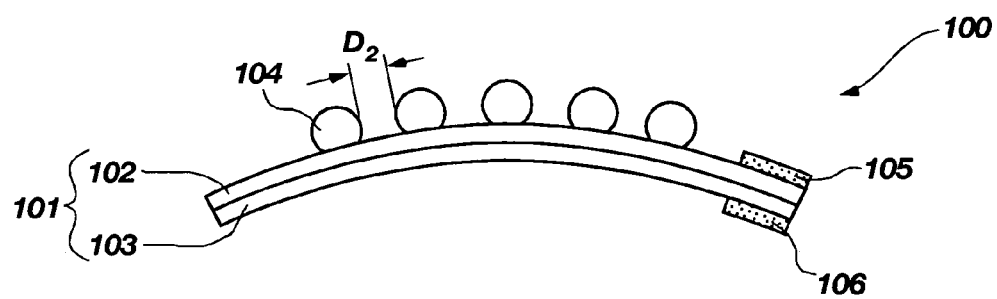
FIG. 9B is a side view of the NERS-active structure shown in FIG. 9A illustrating the deformable substrate in a deformed state.

Another exemplary NERS-active structure 100 that embodies teachings of the present invention is shown in FIGS. 9A-9B. The NERS-active structure 100 includes an elastically deformable dielectric substrate 101 and a plurality of nanoparticles 104 formed from a NERS-active material. The elastically deformable dielectric substrate 101 can be formed from, for example, a first layer of piezoelectric material 102 stacked on top of a second layer of piezoelectric material 103. The first layer of piezoelectric material 102 is oppositely poled relative to the second layer of piezoelectric material 103 to form a cantilever-type piezoelectric bender. A first electrode 105 can be applied to a surface of the first layer of piezoelectric material 102 and a second electrode 106 can be applied to a surface of the second layer of piezoelectric material 103. Each nanoparticle 104 is attached to a surface of the elastically deformable dielectric substrate 101 such that elastic deformation of the dielectric substrate causes the distance between the nanoparticles 104 to change. In this configuration, an active nanoparticle support structure for supporting the plurality of nanoparticles 104 is provided by the elastically deformable dielectric substrate 101.

As shown in FIG. 9A, each nanoparticle 104 is separated from adjacent nanoparticles 104 by a first distance $D_1$ when the dielectric substrate 101 is in a non-deformed state. If the dielectric substrate 101 is bent to a configuration in which the surface of the dielectric substrate 101 on which the nanoparticles 104 are disposed forms a concave surface, as shown in FIG. 9B, each nanoparticle 104 is separated from adjacent nanoparticles 104 by a distance $D_2$, which is greater than the distance $D_1$ shown in FIG. 9A. Alternatively, the dielectric substrate 101 shown in FIG. 9A could be bent to a configuration in which the surface of the dielectric substrate 101 on which the nanoparticles 104 are disposed forms a convex surface. In such a configuration, the distance $D_2$ separating adjacent nanoparticles 104 would be less than the distance $D_1$ shown in FIG. 9A.

Applying a voltage between the first electrode 105 and the second electrode 106 may cause one of the first layer of piezoelectric material 102 or the second layer of piezoelectric material 103 to expand and the other layer of piezoelectric material to contract. This causes the dielectric substrate 101 to bend in a first direction. Reversing the polarity of the voltage may cause the dielectric substrate to bend in the opposite direction.

While the number and size of the nanoparticles 104 shown in FIGS. 9A-9B imply that the size of the dielectric substrate 101 is small, in actuality, the dielectric substrate 101 can be much larger than the nanoparticles 104. For example, the dielectric substrate 101 could be formed from a wafer of silicon, silicon oxide, sapphire, or a polymer material and have millimeter sized dimensions. In this configuration, the dielectric substrate 101 can be bent using simple mechanical or other electromechanical means. In this manner, the NERS-active structure 100 can be used to selectively vary the distance between adjacent nanoparticles 94.

Figure 10A:
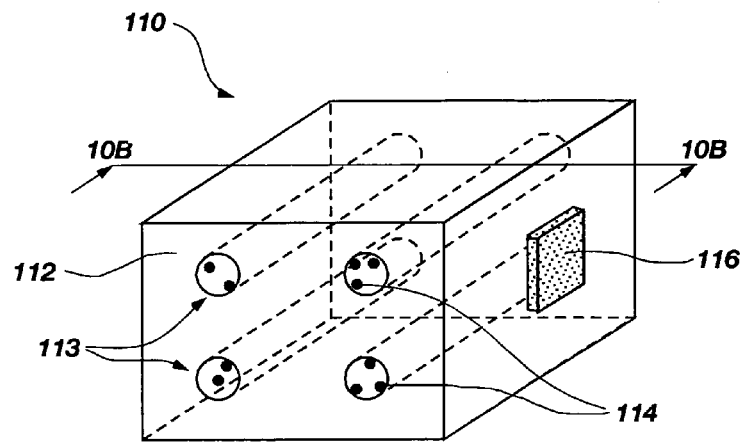
FIG. 10A is a perspective view of an exemplary NERS-active structure that embodies teachings of the present invention and that includes nanoparticles disposed on a deformable substrate.
Figure 10B:
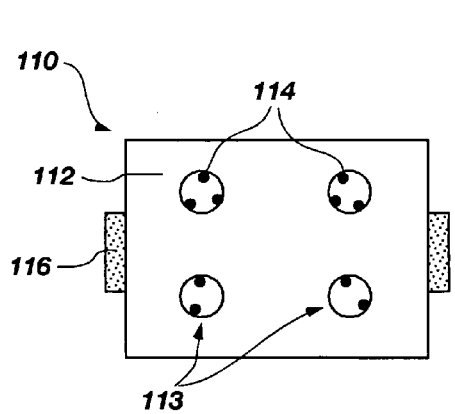
FIG. 10B is a cross sectional view of the NERS-active structure shown in FIG. 10A taken along section line 10B-10B therein.

Another exemplary NERS-active structure 110 that embodies teachings of the present invention is shown in FIGS. 10A-10B. The NERS-active structure 110 includes a three-dimensional elastically deformable dielectric substrate 112 and a plurality of nanoparticles 114 formed from a NERS-active material. The elastically deformable dielectric substrate 112 can be formed from, for example, a piezoelectric material. The NERS-active structure 110 can include electrodes 116 for applying a voltage across the piezoelectric material of the dielectric substrate 112. A plurality of microchannels 113 can be formed through the dielectric substrate 112. As seen in FIG. 10B, each nanoparticle of the plurality of nanoparticles 114 can be disposed on an interior surface of the dielectric substrate 112 within one of the microchannels 113. In this configuration, an active nanoparticle support structure for supporting the plurality of nanoparticles 114 is provided by the elastically deformable dielectric substrate 112.

Figure 10C:
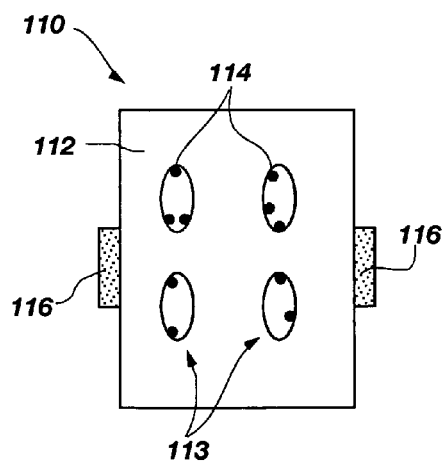
FIG. 10C is a view like that of FIG. 10B showing the deformable substrate in a deformed state.

Applying a voltage across the piezoelectric material may cause the dimensions of the dielectric substrate to change and the shape or size of the microchannels 113 to change. The deformable dielectric substrate 112 is shown in a deformed state in FIG. 10C. As seen therein, deformation of the dielectric substrate 112 causes deformation of the microchannels 113, which changes the distance between the nanoparticles 114 within each microchannel 113.

The NERS-active structure 110 shown in FIGS. 10A-10B can be used to perform NERS on an analyte. The analyte can be provided proximate the nanoparticles 114 within the microchannels 113. The spacing between the nanoparticles 114 then can be varied by applying a voltage across the electrodes 116 while irradiating the analyte and the NERS-active structure 110. If the material used to form the dielectric substrate 112 is not transparent to the incident and scattered radiation, the incident radiation must be directed into the openings of the microchannels 113 and the scattered radiation must be collected from the openings of the microchannels 113. The spacing between the nanoparticles 114 (or the polarity and magnitude of the voltage applied between the electrodes 116) at which the intensity of observed Raman scattered radiation is a maximum can be identified and maintained.

Alternatively, the degree of elastic deformation of the dielectric substrate 112 can be made to oscillate while performing NERS. For example, one electrode 116 can be electrically grounded and a pulsed electrical signal can be applied to the other electrode 116. The pulsed electrical signal may be, for example, sinusoidal, square, or triangular. The characteristics of the electrical signal, such as, for example, amplitude and frequency, can then be adjusted to optimize the intensity of the Raman scattered radiation. By oscillating the degree of elastic deformation of the dielectric substrate 112, a range of distances between the nanoparticles 114 within the microchannels 113 can be provided, some of which may substantially enhance the intensity of Raman scattered radiation. In this manner, the NERS-active structure 110 can be used to selectively vary the distance between adjacent nanoparticles 94.

In another embodiment, the dielectric substrate 112 can be formed from a material other than a piezoelectric material, and the dielectric substrate 112 can be deformed by, for example, applying a load to the dielectric substrate by mechanical means instead of by employing the piezoelectric effect.

Another exemplary NERS-active structure 120 that embodies teachings of the present invention is shown in FIGS. 11A-11B. The NERS-active structure 120 includes a three-dimensional elastically deformable dielectric substrate 122 and a plurality of nanoparticles 124 formed from a NERS-active material. The elastically deformable dielectric substrate 122 can be formed from, for example, a porous material. The porous material can have an open-pore structure, in which the pores 123 form a pathway of interconnecting networked channels through the dielectric substrate 122 between outer surfaces thereof. As seen in FIG. 11B, at least some of the nanoparticles 124 can be disposed on or adjacent to the interior surfaces of the dielectric substrate 122 within the pores 123 thereof.

Alternatively, the porous material can have a closed-pore structure in which continuous pathways are not provided through the structure between surfaces thereof. If the porous material has a closed-pore structure, microchannels such as the microchannels 113 shown in FIGS. 10A-10B can be employed as described previously in relation to the NERS-active structure 110 shown therein.

The substrate 122 of the NERS-active structure 120 shown in FIGS. 11A-11B can be formed from, for example, a polymer material or any elastically deformable dielectric material that is transparent to the wavelengths of radiation to be used to perform NERS. The NERS-active structure 120 can be formed by forming a three dimensional structure comprising nanoparticles 124 dispersed throughout a matrix of elastically deformable dielectric material and subsequently forming pores 123 in the structure. Alternatively, the NERS-active structure 120 can be formed by forming a three dimensional porous structure comprising elastically deformable dielectric material, and subsequently introducing nanoparticles 124 into the porous structure. In this configuration, an active nanoparticle support structure for supporting the plurality of nanoparticles 114 is provided by the elastically deformable dielectric substrate 122.

Deformation of the dielectric substrate 122 may cause deformation of the pores 123, which may change the distance between the nanoparticles 124 within each pore. The deformable dielectric substrate 122 is shown in a deformed state in FIG. 11C. The dielectric substrate 122 can be deformed by, for example, applying a load to the dielectric substrate by, for example, pneumatic, hydraulic, or electro-mechanical means.

The NERS-active structure 120 shown in FIGS. 11A-11B can be used to perform NERS on an analyte. The analyte can be provided proximate to the nanoparticles 124 within the pores 123 of the dielectric substrate 122. The spacing between the nanoparticles 124 can then be varied by applying a load to the dielectric substrate while irradiating the analyte and the NERS-active structure 120. Applying a load to the dielectric substrate 122 may cause deformation of the pores 123, which may change the distance separating adjacent nanoparticles 124 within the pores 123. The spacing between the nanoparticles 124 at which the intensity of observed Raman scattered radiation is a maximum can be identified and maintained.

Alternatively, the degree of elastic deformation of the dielectric substrate 122 can be made to oscillate while performing NERS. By oscillating the degree of elastic deformation of the dielectric substrate 122, a range of distances between the nanoparticles 114 within the pores can be provided, some of which may substantially enhance the intensity of Raman scattered radiation. In this manner, the NERS-active structure 120 can be used to vary the distance between adjacent nanoparticles 124.

In an alternative configuration, the deformable dielectric substrate 122 can be formed from a porous piezoelectric material. Electrodes could be provided for applying a voltage across the piezoelectric material to cause elastic deformation of the dielectric substrate 122.

Figure 12:
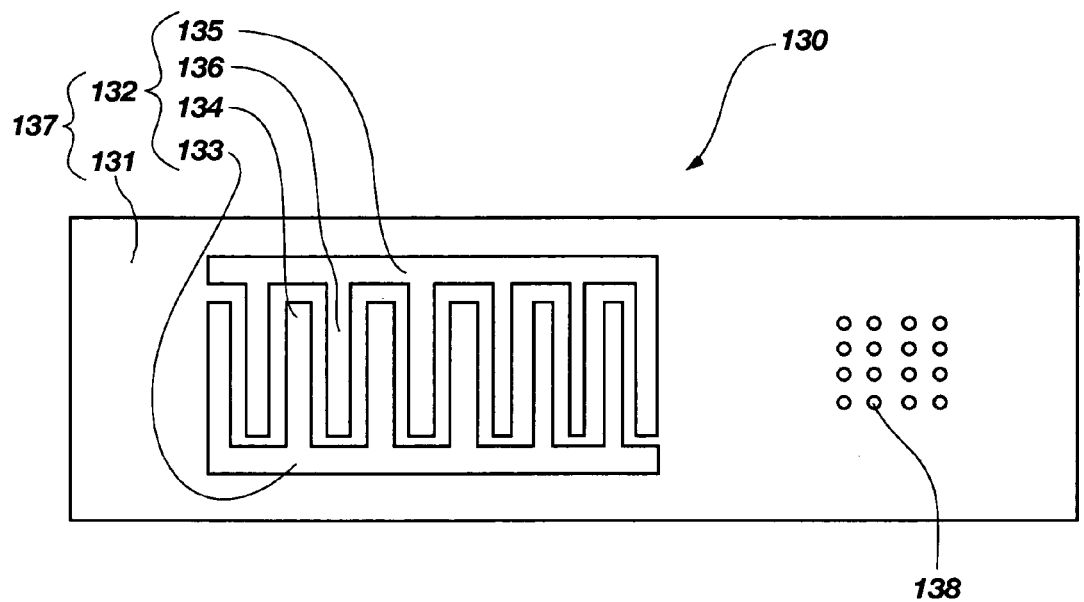
FIG. 12 is a top plan view of an exemplary NERS-active structure that embodies teachings of the present invention and that includes nanoparticles disposed on a deformable substrate and a device for generating surface acoustic waves.

Another exemplary NERS-active structure 130 that embodies teachings of the present invention is shown in FIG. 12. The NERS-active structure 130 includes a surface-acoustic wave (SAW) device 132 formed on a substrate 131. The surface-acoustic wave device 132 is configured to generate elastic mechanical deformation waves in the surface of the substrate 131. The NERS-active structure 130 also includes a plurality of nanoparticles 138. Each nanoparticle 138 can be attached to or formed at a particular location on the surface of the substrate 131 such that deformation of the substrate 131 caused by the surface-acoustic wave device 132 causes the distance separating adjacent nanoparticles 138 to change.

The surface-acoustic wave device 132 can be configured as an inter-digital transducer (IDT). The surface-acoustic wave device 132 can include a first sum line 133 and a second sum line 135 that extend generally parallel to one another along a surface of the substrate 131. A first plurality of digits 134 extends laterally from the first sum line 133 towards the second sum line 135. A second plurality of digits 136 extends laterally from the second sum line 135 towards the first sum line 133, the digits of the second plurality of digits 136 being disposed in the spaces between the digits of the first plurality of digits 134.

The substrate 131 of the NERS-active structure 130 shown in FIG. 12 can be formed from any known piezoelectric material. The nanoparticles 138 are formed from a NERS-active material. The first sum line 133, the first plurality of digits 134, the second sum line 135, and the second plurality of digits 136 can be formed from any conductive material including, but not limited to, silver, gold, copper or other metals.

In this configuration, an active nanoparticle support structure 137 for supporting the plurality of nanoparticles 138 is provided by the surface acoustic wave device 132 and the substrate 131.

Deformation of the substrate 131 at the surface thereon in the region proximate the nanoparticles 138 may change the distance separating adjacent nanoparticles 138. The substrate 131 can be deformed by generating standing or traveling elastic mechanical deformation waves in the surface of the substrate 131 using the surface acoustic wave device 132. To generate standing or traveling elastic mechanical deformation waves in the surface of the substrate 131, a voltage can be applied between the first sum line 133 and the second sum line 135, which provides a voltage between adjacent digits of the first plurality of digits 134 and the second plurality of digits 136. This may generate strains or elastic deformation in the underlying substrate 131, which includes piezoelectric material. If the strains exhibit a proper periodicity, elastic deformation waves can be generated across the surface of the substrate 131 including the region thereof proximate the nanoparticles 138. The characteristics of the surface acoustic waves generated in the surface of the substrate 131, including amplitude and frequency is at least partially a function of the spacing between adjacent digits of the first plurality of digits 134 and the second plurality of digits 136, the pattern formed by the first plurality of digits 134 and the second plurality of digits 136, and the characteristics of the applied voltage.

The NERS-active structure 130 shown in FIG. 12 can be used to perform NERS on an analyte. The analyte can be provided between or proximate to the nanoparticles 138. The spacing between the nanoparticles 138 then can be varied by generating surface acoustic waves in the surface of the substrate 131 using the surface-acoustic wave generating device 132. For example, one of the first sum line 133 and the second sum line 135 may be electrically grounded and a pulsed electrical signal may be applied to the other sum line. The pulsed electrical signal may be, for example, sinusoidal, square, or triangular. The characteristics of the electrical signal, such as, for example, amplitude and frequency, can then be adjusted to optimize the intensity of the Raman scattered radiation. By varying the spacing between adjacent nanoparticles 138, a range of distances between adjacent nanoparticles 138 may be provided, some of which may substantially enhance the intensity of Raman scattered radiation. In this manner, the NERS-active structure 130 can be used to selectively vary the distance between adjacent nanoparticles 138.

Many other structures for surface-acoustic wave generating devices are known in the art and can be adapted to provide a NERS-active structure that embody teachings of the present invention in the manner described in herein in relation to the NERS-active structure 130 shown in FIG. 12.

Each of the NERS-active structures disclosed herein can be formed either on or in a surface of a substrate by known techniques for fabrication of microscale and nanoscale devices. Such techniques include, for example, lithographic techniques for forming layers of material in a surface of a substrate, depositing layers of material on a surface of a substrate, and removing layers of material or regions of layers of material from a surface of a substrate.

Figure 13:
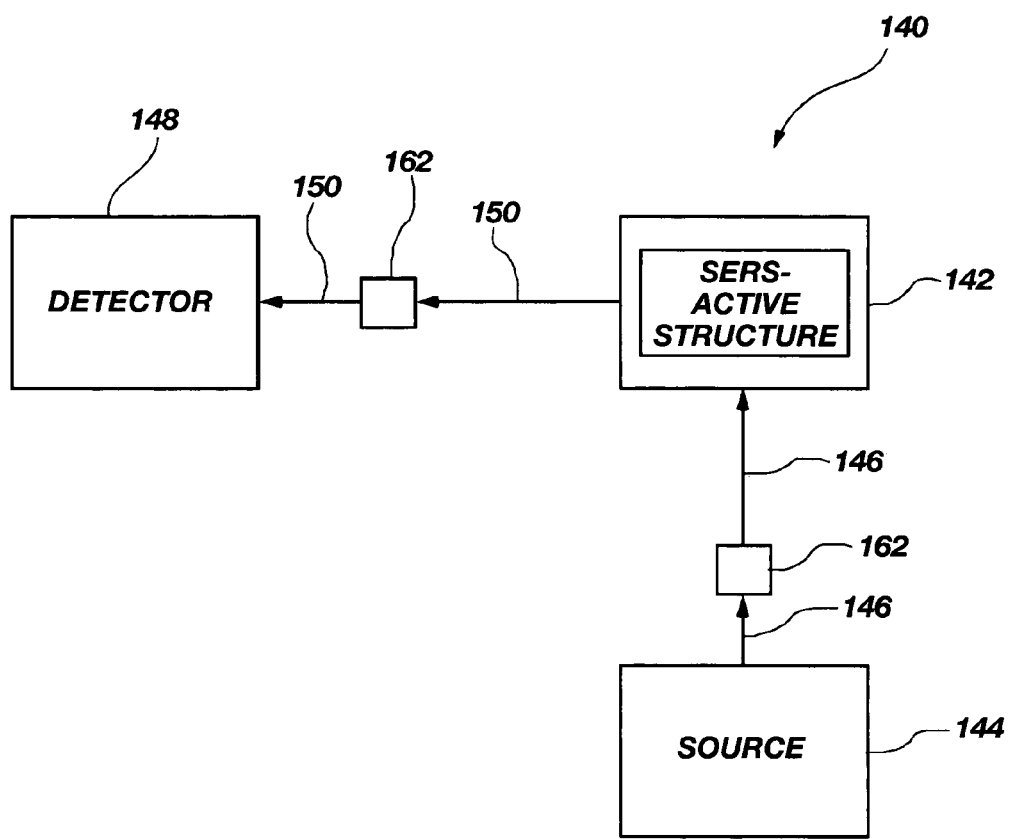
FIG. 13 is a schematic diagram of an exemplary NERS system that embodies teachings of the present invention and that includes a NERS-active structure.

NERS-active structures that embody teachings of the present invention can be used in NERS systems to perform NERS on an analyte. An exemplary NERS system 140 that embodies teachings of the present invention is illustrated schematically in FIG. 13. The NERS system 140 can include an analyte stage 142 for holding a NERS-active structure that embodies teachings of the present invention and the analyte. The NERS system 140 also can include a radiation source 144 for providing incident radiation 146, and a detector 148 for detecting Raman scattered radiation 150. The NERS system 140 also can include various optical components 162, such as, for example, lenses and filters, positioned between the radiation source 144 and the analyte stage 142, and positioned between the analyte stage 142 and the detector 148.

The radiation source 144 can include any suitable source for emitting radiation at the desired wavelength and can be capable of emitting a tunable wavelength of radiation. For example, commercially available semiconductor lasers, helium-neon lasers, carbon dioxide lasers, radiation emitting diodes, incandescent lamps, and many other known radiation emitting sources can be used as the radiation source 144. The wavelengths that are emitted by the radiation source 144 can be any suitable wavelength for performing NERS on the analyte. An exemplary range of wavelengths that can be emitted by the radiation source 144 includes wavelengths between about 350 nanometers and about 1000 nanometers.

The detector 148 receives and detects the Raman scattered radiation 150 generated by Raman scattered photons that are scattered by the analyte. The detector 148 includes a device for determining the wavelength of the Raman scattered radiation 150, such as, for example, a monochromator, and a device for determining the intensity of the Raman scattered radiation 150 such as, for example, a photomultiplier. Typically, the Raman scattered radiation 150 is scattered in all directions relative to the analyte stage 142. Thus, the position of the detector 148 relative to the analyte stage 142 is not particularly important. However, the detector 148 can be positioned at, for example, an angle of 90° relative to the direction of the incident radiation 146 to minimize the intensity of any incident radiation 146 that impinges unintentionally on the detector 148.

Optical components 162 positioned between the source 144 and the analyte stage 142 can be used to collimate, filter, or focus the incident radiation 146 before the incident radiation 146 impinges on the analyte stage 142 and the NERS-active structure. Optical components 162 positioned between the analyte stage 142 and the detector 148 can be used to collimate, filter, or focus the Raman scattered radiation 150. For example, a filter or a plurality of filters can be employed to prevent radiation at wavelengths corresponding to the incident radiation 146 from impinging on the detector 148, thus allowing only the Raman scattered radiation 150 to be received by the detector 148.

To perform NERS using the NERS system 140, the analyte can be provided adjacent the NERS-active structure. The NERS-active structure and the analyte are then irradiated with incident radiation 146 provided by the source 144. Raman scattered radiation 150 scattered by the analyte is detected by the detector 148. The NERS-active structure of the analyte stage 142 enhances the intensity of the Raman scattered radiation 150. The wavelengths and corresponding intensity of the Raman scattered radiation 150 can be determined and used to identify and provide information about the analyte.

The NERS-active structures disclosed herein include an active nanoparticle support structure that is configured to vary the distance between nanoparticles disposed thereon while performing NERS. The active nanoparticle support structure can be configured to provide distances between nanoparticles that can be varied by as little as a few nanometers to as much as a few microns. Typically, the active nanoparticle support structure is configured to provide distances between nanoparticles that can be varied by tens of nanometers.

The ability to vary the distance between nanoparticles is beneficial while performing NERS, since the NERS effect is at least partly dependent upon the spacing between the nanoparticles. The NERS-active structures disclosed herein could be used in spectroscopy techniques other than NERS in which the ability to vary the distance between nanoparticles is beneficial. For example, the NERS-active structures disclosed herein also might be beneficial for use in emission spectroscopy techniques.

The NERS-active structures and NERS-systems disclosed herein allow for improved surface-enhanced Raman spectroscopy techniques and can be employed as analyte substrates to enhance the intensity of Raman scattered radiation scattered by an analyte located adjacent thereto. The performance of molecular sensors, nanoscale electronics, optoelectronics, and other devices employing the Raman effect can be improved by using the NERS-active structures disclosed herein.

Although the foregoing description contains many specifics, these are not to be construed as limiting the scope of the present invention, but merely as providing certain exemplary embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A NERS-active structure comprising:
   a first nanoparticle comprising a NERS-active material;
   a second nanoparticle comprising a NERS-active material, the second nanoparticle being disposed proximate the first nanoparticle and separated from the first nanoparticle by a distance; and
   a deflectable, active nanoparticle support structure for supporting the first nanoparticle and the second nanoparticle, the deflectable, active nanoparticle support structure being configured to vary the distance between the first nanoparticle and the second nanoparticle while performing NERS.

2. A NERS-active structure as recited in claim 1, wherein the deflectable, active nanoparticle support structure comprises:
   a substrate, the first nanoparticle being attached to the substrate; and
   a cantilever member, the second nanoparticle being disposed on an end of the cantilever member and suspended in a movable position relative to the first nanoparticle, whereby deflection of the cantilever member causes the distance between the first nanoparticle and the second nanoparticle to change.

3. A NERS-active structure as recited in claim 2, wherein the cantilever member is electrically isolated from at least a region of the substrate proximate the cantilever member, and wherein a voltage applied between the cantilever member and the at least a region of the substrate generates electrostatic forces that cause the cantilever member to deflect relative to the substrate.

4. A NERS-active structure as recited in claim 2, further comprising an additional cantilever member attached to the substrate, the first nanoparticle being disposed on an end of the additional cantilever member and suspended in a movable position relative to the second nanoparticle, the cantilever member being electrically isolated from the additional cantilever member, whereby a voltage applied between the cantilever member and the additional cantilever member generates electrostatic forces that cause both the cantilever member and the additional cantilever member to deflect and the distance between the first nanoparticle and the second nanoparticle to change.

5. A NERS-active structure as recited in claim 1, wherein the deflectable, active nanoparticle support structure comprises:
   a substrate, the first nanoparticle being attached to the substrate; and
   a deflectable bridge-type beam member, the second nanoparticle being disposed on the bridge-type beam member and suspended in a movable position relative to the first nanoparticle, whereby deflection of the bridge-type beam member causes the distance between the first nanoparticle and the second nanoparticle to change.

6. A NERS-active structure as recited in claim 1, wherein the deflectable, active nanoparticle support structure comprises:
   a first plate-shaped member providing a first surface, the first nanoparticle being disposed on the first surface of the first plate-shaped member;
   a thin deflectable second plate-shaped member providing a second surface, the second plate-shaped member being disposed proximate the first plate-shaped member, the first surface being opposed to the second surface and separated therefrom by a distance, the second nanoparticle being disposed on the second surface of the second plate-shaped member; and
   at least one support spacer disposed between the first plate-shaped member and the second plate-shaped member, whereby deflection of the second plate-shaped member relative to the first plate-shaped member causes the distance between the first nanoparticle and the second nanoparticle to change.

7. A NERS-active structure as recited in claim 6, wherein the at least one support spacer is electrically insulating, whereby a voltage applied between the first plate-shaped member and the second plate-shaped member generates electrostatic forces that cause the second plate-shaped member to deflect relative to the first plate-shaped member.

8. A NERS-active structure comprising:
   a first nanoparticle comprising a NERS-active material;
   a second nanoparticle comprising a NERS-active material, the second nanoparticle being disposed proximate the first nanoparticle and separated from the first nanoparticle by a distance
   a static base member, the first nanoparticle being disposed on the static base member;
   a movable base member attached to the static base member, the second nanoparticle being disposed on the movable base member; and
   means for moving the movable base member relative to the static base member, thereby causing the distance between the first nanoparticle and the second nanoparticle to vary.

9. A NERS-active structure as recited in claim 8, wherein the NERS-active structure further comprises:
   a first plurality of generally aligned digit members extending from the static base member; and
   a second plurality of generally aligned digit members extending from the movable base member, each digit member of the second plurality of digit members being disposed in spaces between the digit members of the first plurality of digit members to form an inter-digital structure, the first nanoparticle being disposed on a digit of the first plurality of digit members, the second nanoparticle being disposed on a digit of the second plurality of digit members.

10. A NERS-active structure as recited in claim 8, wherein the movable base member comprises a cantilever member, a bridge-type beam member, or a deflectable plate-shaped member.

11. A NERS system comprising:
   a NERS-active structure comprising:
      a first nanoparticle comprising a NERS-active material;
      a second nanoparticle comprising a NERS-active material, the second nanoparticle being disposed proximate the first nanoparticle and separated from the first nanoparticle by a distance; and
      a movable, active nanoparticle support structure for supporting the first nanoparticle on a first structure member and the second nanoparticle, on a second structure member, the movable active nanoparticle support structure being configured to vary the distance between the first nanoparticle and the second nanoparticle;
   a radiation source for generating radiation scatterable by an analyte located proximate the NERS-active structure; and
   a radiation detector for detecting Raman scattered radiation scattered by the analyte.

12. A NERS system as recited in claim 11, wherein the movable, active nanoparticle support structure of the NERS-active structure comprises:
   a substrate, the first nanoparticle being attached to the substrate; and
   a cantilever member, the second nanoparticle being disposed on an end of the cantilever member and suspended in a movable position relative to the first nanoparticle, whereby deflection of the cantilever member causes the distance between the first nanoparticle and the second nanoparticle to change.

13. A NERS system as recited in claim 11, wherein the movable, active nanoparticle support structure of the NERS-active structure comprises:
   a first plate-shaped member providing a first active surface, the first nanoparticle being disposed on the first active surface;
   a deflectable thin second plate-shaped member providing a second active surface, the second plate-shaped member being disposed proximate the first plate-shaped member, the first active surface being opposed to the second active surface and separated therefrom by a distance, the second nanoparticle being disposed on the second active surface of the second plate-shaped member; and
   at least one support spacer disposed between the first plate-shaped member and the thin second plate-shaped member, whereby deflection of the thin second plate-shaped member relative to the first plate-shaped member causes the distance between the first nanoparticle and the second nanoparticle to change.

14. A NERS system as recited in claim 13, wherein the at least one support spacer of the movable, active nanoparticle support structure is electrically insulating, whereby a voltage applied between the first plate-shaped member and the thin second plate-shaped member generates electrostatic forces that cause the thin second plate-shaped member to deflect relative to the first plate-shaped member.

15. A NERS system as recited in claim 11, wherein the movable, active nanoparticle support structure of the NERS-active structure comprises:
   a static base member, the first nanoparticle being disposed on the static base member;
   a movable base member electrically isolated from the static base member, the second nanoparticle being disposed on the movable base member and separated from the first nanoparticle by a distance; and
   means for generating electrostatic forces that cause the movable base member to move relative to the static base member, whereby movement of the movable base member relative to the static base member causes the distance between the first nanoparticle and the second nanoparticle to vary.

16. A NERS system as recited in claim 15, wherein the movable, active nanoparticle support structure of the NERS-active structure further comprises:
   a first plurality of generally aligned digit members extending from the static base member; and
   a second plurality of generally aligned digit members extending from the movable base member, each digit member of the second plurality of digit members being disposed in spaces between the digit members of the first plurality of digit members to form an inter-digital structure, the first nanoparticle being disposed on a digit of the first plurality of digit members, the second nanoparticle being disposed on a digit of the second plurality of digit members.

17. A NERS system as recited in claim 11, wherein the movable, active nanoparticle support structure of the NERS-active structure comprises an elastically deflectable dielectric substrate, the first nanoparticle and the second nanoparticle being disposed on a surface of the dielectric substrate, the first nanoparticle and the second nanoparticle being separated by a distance, whereby elastic deformation of the dielectric substrate causes the distance between the first nanoparticle and the second nanoparticle to change.

18. A NERS system as recited in claim 17, wherein the deformable dielectric substrate comprises silica, sapphire, or a polymer material.

19. A NERS system as recited in claim 17, wherein the movable, active nanoparticle support structure further comprises a piezoelectric device, the dielectric substrate being disposed on a surface of the piezoelectric device, whereby deformation of the piezoelectric device causes deformation of the dielectric substrate.

20. A NERS system as recited in claim 17, wherein the elastically deflectable dielectric substrate of the movable, active nanoparticle support structure is porous, the first nanoparticle and the second nanoparticle being disposed on an interior surface of the dielectric substrate within a pore of the dielectric substrate.

21. A NERS system as recited in claim 20, wherein the porous dielectric substrate has an open pore structure.

22. A NERS system as recited in claim 17, wherein the dielectric substrate is configured as a three-dimensional structure, the dielectric substrate further comprising at least one microchannel formed through the dielectric substrate, the first nanoparticle and the second nanoparticle being disposed on an interior surface of the dielectric substrate within the at least one microchannel.

23. A NERS system as recited in claim 17, wherein the movable, active nanoparticle support structure further comprises an elastic mechanical-deformation wave-generating device attached to the dielectric substrate for generating elastic mechanical-deformation waves in the dielectric substrate to vary the distance between the first nanoparticle and the second nanoparticle.

24. A method for performing NERS comprising:
   providing a NERS-active structure comprising:
      a first nanoparticle comprising a NERS-active material;

a second nanoparticle comprising a NERS-active material, the second nanoparticle being disposed proximate the first nanoparticle and separated from the first nanoparticle by a distance; and a static base member, the first nanoparticle being disposed on the static base member;

a movable base member that is electrical isolated from the static base member, the second nanoparticle being disposed on the movable base member and separated from the first nanoparticle by a distance; and means for generating electrostatic forces that cause the movable base member to move relative to the static base member, whereby movement of the movable base member relative to the static base member causes the distance between the first nanoparticle and the second nanoparticle to vary;

providing an analyte at a location proximate the NERS-active structure;

irradiating the NERS-active structure and the analyte with radiation;

varying the distance between the first nanoparticle and the second nanoparticle; and detecting Raman scattered radiation scattered by the analyte.

25. A method for performing NERS as recited in claim 24, wherein the means for generating electrostatic forces comprises means for applying a voltage between the static base member and the movable base member.

26. A method for performing NERS as recited in claim 25, wherein varying the distance between the first nanoparticle and the second nanoparticle comprises applying a voltage between the static base member and the movable base member.

27. A method for performing NERS as recited in claim 26, wherein applying a voltage comprises grounding one of the static base member and the moveable base member and applying an electrical signal to the other one of the static base member and the moveable base member applying an electrical signal comprises applying a pulsed electrical signal.

28. A method for performing NERS as recited in claim 27, wherein applying an electrical signal comprises applying a pulsed electrical signal, the pulsed electrical signal being sinusoidal, square, or triangular electrical signal.

29. A method for performing NERS as recited in claim 27, further comprising tuning the electrical signal to maximize the amount of detected Raman scattered radiation.

30. A method for performing NERS as recited in claim 24, wherein providing a movable base member comprises providing a cantilever member, a bridge-type beam member, a deflectable plate-shaped member, or part of an inter-digital structure.

31. A method for performing NERS as recited in claim 24, wherein the deflectable, active nanoparticle support structure comprises an elastically deflectable dielectric substrate, the first nanoparticle and the second nanoparticle being disposed on a surface of the dielectric substrate, the first nanoparticle and the second nanoparticle being separated by a distance, whereby elastic deformation of the dielectric substrate causes the distance between the first nanoparticle and the second nanoparticle to change.

* * * * *

UNITED STATES PATENT AND TRADEMARK OFFICE
CERTIFICATE OF CORRECTION

PATENT NO. : 7,342,656 B2 Page 1 of 1
APPLICATION NO. : 11/252134
DATED : March 11, 2008
INVENTOR(S) : M. Saif Islam et al.

It is certified that error appears in the above-identified patent and that said Letters Patent is hereby corrected as shown below:

In column 25, line 14, in Claim 11, after "nanoparticle" delete ",".

In column 25, line 15, in Claim 11, after "movable" insert -- , --.

In column 26, line 27, in Claim 17, delete "deflectable" and insert -- deformable --, therefor.

In column 26, line 44, in Claim 20, delete "deflectable" and insert -- deformable --, therefor.

In column 27, line 7, in Claim 24, delete "electrical" and insert -- electrically --, therefor.

Signed and Sealed this

Fourteenth Day of July, 2009

JOHN DOLL
*Acting Director of the United States Patent and Trademark Office*